(12) United States Patent
Rosen et al.

(10) Patent No.: US 6,287,816 B1
(45) Date of Patent: *Sep. 11, 2001

(54) BMP-9 COMPOSITIONS

(75) Inventors: Vicki A. Rosen, Brookline; John M. Wozney; Anthony J. Celeste, both of Hudson; R. Scott Thies, Andover; Jeffrey R. Song, Brookline, all of MA (US)

(73) Assignee: Genetics Institute, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/254,353

(22) Filed: Jun. 6, 1994

Related U.S. Application Data

(63) Continuation-in-part of application No. 08/050,132, filed on Apr. 22, 1993, now Pat. No. 5,661,007, which is a continuation-in-part of application No. 07/720,590, filed on Jun. 25, 1991, now abandoned.

(30) Foreign Application Priority Data

Jun. 25, 1992 (WO) .................................. PCT/US92/05374

(51) Int. Cl.[7] .......................... C12P 21/00; A61K 38/18; A61K 9/00; C07K 14/51
(52) U.S. Cl. ................. 435/69.4; 435/320.1; 435/252.3; 435/325; 530/399; 530/840; 930/120; 514/12; 424/423; 424/426; 424/484; 536/24.31; 536/23.51
(58) Field of Search .................................... 530/399, 840; 930/120; 514/12; 424/423, 426, 484; 435/69.4, 240.2, 320.1, 252.3, 325; 536/24.31, 23.51

(56) References Cited

U.S. PATENT DOCUMENTS

| 4,294,753 | 10/1981 | Urist ..................................... 530/395 |
|---|---|---|
| 4,434,094 | 2/1984 | Seyedin et al. ..................... 530/416 |

(List continued on next page.)

FOREIGN PATENT DOCUMENTS

| 2 017466 | 5/1990 | (CA) . |
|---|---|---|
| 33 6760 | 6/1989 | (EP) . |
| 4 165 78A2 | 5/1990 | (EP) . |
| 4 094 72 A1 | 11/1990 | (EP) . |
| WO 89/09787 | 10/1989 | (WO) . |
| WO 89/09788 | 10/1989 | (WO) . |
| WO 90/03733 | 4/1990 | (WO) . |
| WO 91/02744 | 3/1991 | (WO) . |
| WO 91/05802 | 5/1991 | (WO) . |
| WO 91/18047 | 11/1991 | (WO) . |
| WO 92/07004 | 4/1992 | (WO) . |
| WO 92/07073 | 4/1992 | (WO) . |
| WO 93/04692 | 3/1993 | (WO) . |
| WO 93/05751 | 4/1993 | (WO) . |

OTHER PUBLICATIONS

Sporn et al. 1988. Peptide growth factors are multifunctional. Nature, vol. 332, pp. 217–219, Mar. 1988.*

Baird et al. 1986. Inhbibition of endothelial cell proliferation by type–beta transforming growth factor: interactions with acidic and basic fibroblast growth factors. Biochem. Biophys. Res. Commun. vol. 138, pp. 476–482, Jul. 1986.*

(List continued on next page.)

*Primary Examiner*—David Romeo
(74) *Attorney, Agent, or Firm*—Ellen J. Kapinos

(57) ABSTRACT

Purified bone morphogenetic protein-9 (BMP-9) proteins and processes for producing them are disclosed. The proteins may be used in the treatment of bone and cartilage defects and in wound healing and related tissue repair.

29 Claims, 16 Drawing Sheets

U.S. PATENT DOCUMENTS

| | | | |
|---|---|---|---|
| 4,455,256 | 6/1984 | Urist | 530/350 |
| 4,563,350 | 1/1986 | Nathan | 424/95 |
| 4,608,199 | 8/1986 | Caplan et al. | 530/414 |
| 4,619,989 | 10/1986 | Urist | 530/417 |
| 4,627,982 | 12/1986 | Seyedin et al. | 424/95 |
| 4,681,763 | 7/1987 | Nathanson | 424/95 |
| 4,737,578 | 4/1988 | Evans | 530/350 |
| 4,761,471 | 8/1988 | Urist | 530/350 |
| 4,774,228 | 9/1988 | Seyedin | 514/21 |
| 4,774,322 | 9/1988 | Seyedin | 530/353 |
| 4,789,732 | 12/1988 | Urist | 530/350 |
| 4,795,804 | 1/1989 | Urist | 530/350 |
| 4,798,885 | 1/1989 | Mason | 530/350 |
| 4,804,744 | 2/1989 | Sen | 530/350 |
| 4,810,691 | 3/1989 | Seyedin | 514/2 |
| 4,843,063 | 6/1989 | Seyedin | 514/2 |
| 4,886,747 | 12/1989 | Derynck | 435/69.4 |
| 4,968,590 | 11/1990 | Kuberasampath et al. | 530/326 |
| 5,011,691 | 4/1991 | Oppermann | 424/423 |
| 5,106,626 | 4/1992 | Parsons et al. | 424/423 |
| 5,108,753 | 4/1992 | Kuberasampath | 424/422 |
| 5,168,050 * | 12/1992 | Hammonds, Jr. et al. | 435/69.1 |
| 5,661,007 * | 8/1997 | Wozney et al. | 435/69.4 |

OTHER PUBLICATIONS

Roberts et al. 1986. Tranforming growth factor type–beta: rapid induction of fibrosis and angiogenesis in vivo and stimulation of collagen formation in vitro. Proc. Natl. Acad. Sci. USA, vol. 83, pp. 4167–4171, Jun. 1986.*

Shipley et al. 1986. Reversible inhition of normal human prokeratinocyte proliferation by type beta transforming growth factor–gorwth inhibitor in serum–free medium. Cancer Res., vol. 46, pp. 2068–2071, Apr. 1986.*

Beck et al. 1990. Accelerated healing of ulcer wounds in the rabbit ear by recombinant human transforming grrowth–beta 1. Growth Factors, vol. 2, pp. 273–282, Feb. 1990.*

Hebda et al. 1988. Stimulatory effects of transforming growth factor–beta and epidermal growth factor on epidermal cell outgrowth from porcine skin expalnt cultures. J. Invest. Dermatol., vol. 91, pp. 440–445, Nov. 1988.*

McDonald et al. 1993. A structural superfamily of growth factors containing a cystine knot motif. Cell, vol. 73, pp. 421–424, May 1993.*

Wozney et al. 1988. Novel regulators of bone formation: molecular clones and activities. Science, (Dec. 16, 1988) 242 (4885) 1528–1534.*

Wang et al. 1990. Recombinant human bone morphogenetic protein induces bone formation. Proc. Natl. Acad. Sci. U.S.A., vol. 187, pp. 2220–2224, Mar. 1990.*

Sambrook et al. Molecular Cloning: A Laboratory Manual Second Edition vol. 1, 2 and 3. Cold Spring Harbor Laboratory Press: Cold Spring Harbor, New York, U.S.A. Nov. 1989.*

Bowie et al. Deciphering the message in protein sequences: tolerance to amino acid substitutions. Science, (Mar. 16, 1990) 247 (4948) 1306–10.*

Celeste et al "Identification of Transforming Growth Factor B Family Members . . . " *PNAS* 87:9843–9847, Dec. 1990.*

Wozney et al "Novel Regulator of Bone Formation . . . " *Science* 242:1528–1534, Dec. 1988.*

Burt et al, "Evolutionary Grouping of the Transforming Growth Factor–B Superfamily", BBRC 184(2): 590–595, Apr. 1992.*

Wozney et al, "Growth Factors Influencing Bone Development" *J. Cell Sci. Suppl.* 13: 149–156, 1990.*

Wang et al "Recombinant Human Bone Morphogenetic Protein . . . " *PNAS* 87:2220–2224, Mar. 1990.*

Urist et al., *Science* 220: 680–686 (1983).

Luyten et al., *The Journal of Biological Chemistry* 264(23):13377–13380 (1989).

Sampath et al., *Proc. Natl. Acad. Sci* 84:7109–7113 (1987).

Ozkaynak et al., *The EMBO Journal v.9 No.7*:2085–2093 (1990).

Hammonds et al., *Molecular Endocrinology* 5:149–155 (1991).

Celeste et al.,*J. of Bone Mineral Res. v.9 suppl. 5136* (1994).

Celeste et al., *Proc. Natl. Acad. Sci.* 87:9843–9847 (1990).

Wozney et al., *Science* 242:1528–1534 (1988).

Burt et al., *BBRC* 184(2):590–595 (1992).

Wozney et al., *J. Cell Sci. Suppl.* 13:149–156 (1990).

Wang et al., *Proc. Natl.. Acad. Sci.* 87:2220–2224 (1990).

Leslie M. Hyaluronic acid treatment for osteoarthritis of the knee. Nurse Practitioner, (Jul. 1999) 24 (7) 38, 41–8.*

Peyron J G. Is osteoarthritis a preventable disease?. Journal of Rheumatology. Supplement, (Feb. 1991) 27 2–3.*

Lodish et al. Molecular Cell Biology, 3rd edition, Mar. 1995, W. H. Freeman & Co. p. 196.*

Lyons et al. Proc. Natl. Acad. Sci. USA, vol. 86, polypeptide. 4554–4558, Jun. 1989.*

* cited by examiner

Figure 1/1

```
        10          20          30          40          50          60          70
CATTAATAAA  TATTAAGTAT  TGGAATTAGT  GAAATTGGAG  TTCCTTGTGG  AAGGAAGTGG  GCAAGTGAGC
        80          90         100         110         120         130         140
TTTTTAGTTT  GTGTCGGAAG  CCTGTAATTA  CGGCTCCAGC  TCATAGTGGA  ATGGCTATAC  TTAGATTTAT
       150         160         170         180         190         200         210
GGATAGTTGG  GTAGTAGGTG  TAAATGTATG  TGGTAAAAGG  CCTAGGAGAT  TTGTTGATCC  AATAAATATG
       220         230         240         250         260         270         280
ATTAGGGAAA  CAATTATTAG  GGTTCATGTT  CGTCCTTTTG  GTGTGTGGAT  TAGCATTATT  TGTTTGATAA
       290         300         310         320         330         340         350
TAAGTTTAAC  TAGTCAGTGT  TGGAAAGAAT  GGAGACGGTT  GTTGATTAGG  CGTTTTGAGG  ATGGGAATAG
       360         370         380         390         400         410         420
GATTGAAGGA  AATATAATGA  TGGCTACAAC  GATTGGGAAT  CCTATTATTG  TTGGGGTAAT  GAATGAGGCA
       430         440         450         460         470         480         490
AATAGATTTT  CGTTCATTTT  AATTCTCAAG  GGGTTTTTAC  TTTTATGTTT  GTTAGTGATA  TTGGTGAGTA
       500         510         520         530         540         550         560
GGCCAAGGGT  TAATAGTGTA  ATTGAATTAT  AGTGAAATCA  TATTACTAGA  CCTGATGTTA  GAAGGAGGGC
       570         580         590         600         609                  618
TGAAAAGGCT  CCTTCCCTCC  CAGGACAAAA  CCGGAGCAGG  GCCACCCGG ATG TCC CCT GGG
                                                    >———————————————————
                                                         M   S   P   G
```

Figure 1/2

```
     627        636        645        654        663        672
      |          |          |          |          |          |
GCC TTC CGG GTG GCC CTG CTC CCG CTG TTC CTG CTG GTC TGT GTC ACA CAG CAG
 A   F   R   V   A   L   L   P   L   F   L   L   V   C   V   T   Q   Q 681        690        699        708        717        726
      |          |          |          |          |          |
AAG CCG CTG CAG AAC TGG GAA CAA GCA TCC CCT GGG GAA AAT GCC CAC AGC TCC
 K   P   L   Q   N   W   E   Q   A   S   P   G   E   N   A   H   S 735        744        753        762        771        780
      |          |          |          |          |          |
CTG GGA TTG TCT GGA GCT GAG GAG GGT GTC TTT GAC CTG CAG ATG TTC CTG
 L   G   L   S   G   A   E   E   G   V   F   D   L   Q   M   F   L 789        798        807        816        825        834
      |          |          |          |          |          |
GAG AAC ATG AAG GTG GAT TTC CTA CGC AGC CTT AAC CTC GAC AGC GGC ATT CCC TCC
 E   N   M   K   V   D   F   L   R   S   L   N   L   D   S   G   I   P   S
```

Figure 1/3

```
     843         852         861         870         879         888
      |           |           |           |           |           |
CAG GAC AAA ACC AGA GCG GAG CCA CCC CAG TAC ATG ATC GAC TTG TAC AAC AGA
 Q   D   K   T   R   A   E   P   P   Q   Y   M   I   D   L   Y   N   R 897         906         915         924         933         942
      |           |           |           |           |           |
TAC ACA ACG GAC AAA TCG TCT ACG CCT GCC TCC AAC ATC GTG CGG AGC TTC AGC
 Y   T   T   D   K   S   S   T   P   A   S   N   I   V   R   S   F   S 951         960         969         978         987         996
      |           |           |           |           |           |
GTG GAA GAT GCT ATA TCG ACA GCT GCC ACG GAG GAC TTC CCC TTT CAG AAG CAC
 V   E   D   A   I   S   T   A   A   T   E   D   F   P   F   Q   K   H 1005        1014        1023        1032        1041        1050
      |           |           |           |           |           |
ATC CTG ATC TTC AAC ATC TCC ATC CCG AGG CAC GAG CAG ATC ACC AGG GCT GAG
 I   L   I   F   N   I   S   I   P   R   H   E   Q   I   T   R   A   E
```

Figure 1/4

```
     1059        1068        1077        1086        1095        1104
      |           |           |           |           |           |
CTC  CGA  CTC  TAT  GTC  TCC  TGC  CAA  AAT  GAT  GTG  GAC  TCC  ACT  CAT  GGG  CTG  GAA
 L    R    L    Y    V    S    C    Q    N    D    V    D    S    T    H    G    L    E 1113        1122        1131        1140        1149        1158
      |           |           |           |           |           |
GGA  AGC  ATG  GTC  GTT  TAT  GAT  GTT  CTG  GAG  GAC  AGT  GAG  ACT  TGG  GAC  CAG  GCC
 G    S    M    V    V    Y    D    V    L    E    D    S    E    T    W    D    Q    A 1167        1176        1185        1194        1203        1212
      |           |           |           |           |           |
ACG  GGG  ACC  AAG  ACC  TTC  TTG  GTA  TCC  CAG  GAC  ATT  CGG  GAC  GAA  GGA  TGG  GAG
 T    G    T    K    T    F    L    V    S    Q    D    I    R    D    E    G    W    E 1221        1230        1239        1248        1257        1266
      |           |           |           |           |           |
ACT  TTA  GAA  GTA  TCG  AGT  GCC  GTG  AAG  CGG  TGG  GTC  AGG  GCA  GAC  TCC  ACA  ACA
 T    L    E    V    S    S    A    V    K    R    W    V    R    A    D    S    T    T
```

Figure 1/5

```
        1275        1284        1293        1302        1311        1320
         |           |           |           |           |           |
AAC AAA AAT AAG CTC GAG GTG ACA CAG AGC CAC AGG GAG AGC TGT GAC ACA
 N   K   N   K   L   E   V   T   Q   S   H   R   E   S   C   D   T 1329        1338        1347        1356        1365        1374
         |           |           |           |           |           |
CTG GAC ATC AGT GTC CCT CCA GGT TCC AAA AAC CTG CCC TTC TTT GTT GTC TTC
 L   D   I   S   V   P   P   G   S   K   N   L   P   F   F   V   V   F 1383        1392        1401        1410        1419        1428
         |           |           |           |           |           |
TCC AAT GAC CGC AGC AAT GGG ACC AAG GAG ACC AGA CTG GAG CTG AAG GAG ATG
 S   N   D   R   S   N   G   T   K   E   T   R   L   E   L   K   E   M 1437        1446        1455        1464        1473        1482
         |           |           |           |           |           |
ATC GGC CAT GAG CAG GAG ACC ATG CTT GTG AAG ACA GCC AAA AAT GCT TAC CAG
 I   G   H   E   Q   E   T   M   L   V   K   T   A   K   N   A   Y   Q
```

Figure 1/6

```
      1491      1500      1509      1518      1527      1536
       |         |         |         |         |         |
      GTG GCA GGT GAG AGC CAA GAG GAG GGT CTA GAT GGA TAC ACA GCT GTG GGA
       V   A   G   E   S   Q   E   E   G   L   D   G   Y   T   A   V   G 1545      1554      1563      1572      1581      1590
       |         |         |         |         |         |
      CCA CTT TTA GCT AGA AGG AAG AGC ACC GGA GCC AGC AGC CAC TGC CAG AAG
       P   L   L   A   R   R   K   S   T   G   A   S   S   H   C   Q   K
                          (319)                           (326)

1599      1608      1617      1626      1635      1644
       |         |         |         |         |         |
      ACT TCT CTC AGG GTG AAC TTT GAG GAC ATC GGC TGG GAC AGC TGG ATC ATT GCA
       T   S   L   R   V   N   F   E   D   I   G   W   D   S   W   I   I   A 1653      1662      1671      1680      1689      1698
       |         |         |         |         |         |
      CCC AAG GAA TAT GAC GCC TAT GAG TGT AAA GGG GGT TGC TTC TTC CCA TTG GCT
       P   K   E   Y   D   A   Y   E   C   K   G   G   C   F   F   P   L   A
```

Figure 1/7

```
     1707      1716      1725      1734      1743      1752
       |         |         |         |         |         |
     GAT GAC GTG ACA CCC ACC AAA CAT GCC ATC GTG CAG ACC CTG GTG CAT CTC GAG
      D   D   V   T   P   T   K   H   A   I   V   Q   T   L   V   H   L   E 1761      1770      1779      1788      1797      1806
       |         |         |         |         |         |
     TTC CCC ACA AAG GTG GGC AAA GCC TGC TGC GTT CCC ACC AAA CTG AGT CCC ATC
      F   P   T   K   V   G   K   A   C   C   V   P   T   K   L   S   P   I 1815      1824      1833      1842      1851      1860
       |         |         |         |         |         |
     TCC ATC CTC TAC AAG GAT GAC ATG GGG GTG CCA ACC CTC AAG TAC CAC TAT GAG
      S   I   L   Y   K   D   D   M   G   V   P   T   L   K   Y   H   Y   E 1869      1878      1887                    1903      1913      1923
       |         |         |                       |         |         |
     GGG ATG AGT GTG GCT GAG TGT TGT AGG TAGTCCCTGC AGCCACCCAG GGTGGGGATA
      G   M   S   V   A   E   C   C   R
                                 (428)
```

Figure 1/8

```
           1933       1943       1953       1963       1973       1983       1993
     CAGGACATGG AAGAGGTTCT GGTACGGTCC TGCATCCTCC TGCGCATGGT ATGCCTAAGT TGATCAGAAA
           2003       2013       2023       2033       2043       2053       2063
     CCATCCTTGA GAAGAAAAGG AGTTAGTTGC CCTTCTGTGT TCTGGTGGGT CCCTCTGCTG AAGTGACAAT
           2073       2083       2093       2103       2113       2123       2133
     GACTGGGGTA TGCGGGCCTG TGGGCAGAGC AGGAGACCCT GGAAGGGTTA GTGGGTAGAA AGATGTCAAA
           2143       2153       2163       2173       2183       2193       2203
     AAGGAAGCTG TGGGTAGATG ACCTGCACTC CAGTGATTAG AAGTCCAGCC TTACCTGTGA GAGAGCTCCT
           2213       2223       2233       2243       2253       2263       2273
     GGCATCTAAG AGAACTCTGC TTCCTCATCA TCCCCACCGA CTTGTTCTTC CTTGGGAGTG TGTCCTCAGG
           2283       2293       2303       2313       2323       2333       2343
     GAGAACAGCA TTGCTGTTCC TGTGCCTCAA GCTCCCAGCT GACTCTCCTG TGGCTCATAG GACTGAATGG
           2353       2363       2373       2383       2393       2403       2413
     GGTGAGGAAG AGCCTGATGC CCTCTGGCAA TCAGAGCCCG AAGGACTTCA AAACATCTGG ACAACTCTCA
           2423       2433       2443
     TTGACTGATG CTCCAACATA ATTTTTAAAA AGAG
```

Figure 2/1

```
         10           20           30           40           50           60           70
CTCTAGAGGG   CAGAGGAGGA   GGGAGGGAGG   GAAGGAGCGC   GGAGCCCGC    CCGGAAGCTA   GGTGAGTGTG 80           90          100          110          120          130          140
GCATCCGAGC   TGAGGGACGC   GAGCCTGAGA   CGCCGCTGCT   GCTCCGGCTG   AGTATCTAGC   TTGTCTCCCC 150          160          170          180          190          200          210
GATGGGATTC   CCGTCCAAGC   TATCTCGAGC   CTGCAGCGCC   ACAGTCCCCG   GCCCTCGCCC   AGGTTCACTG 220          230          240          250          260          270          280
CAACCGTTCA   GAGGTCCCCA   GGAGCTGCTG   CTGGCGAGCC   CGCTACTGCA   GGGACCTATG   GAGCCATTCC 290          300          310          320          330          340          350
GTAGTGCCAT   CCCGAGCAAC   GCACTGCTGC   AGCTTCCCTG   AGCCTTTCCA   GCAAGTTTGT   TCAAGATTGG 360          370          380          390         400      (1)
CTGTCAAGAA   TCATGGACTG   TTATTATATG   CCTTGTTTTC   TGTCAAGACA   CC ATG ATT CCT
                                                                    MET Ile Pro 417           432             447                462
GGT AAC CGA ATG CTG ATG GTC GTT TTA TTA TGC CAA GTC CTG CTA GGA GGC GCG
Gly Asn Arg MET Leu MET Val Val Leu Leu Cys Gln Val Leu Leu Gly Gly Ala
```

Figure 2/2

```
                477                  492                  507
AGC CAT GCT AGT TTG ATA CCT GAG ACG GGG AAG AAA AAA GTC GCC GAG ATT CAG
Ser His Ala Ser Leu Ile Pro Glu Thr Gly Lys Lys Lys Val Ala Glu Ile Gln 522                  537                  552                567
GGC CAC GCG GGA GGA CGC CGC TCA GGG CAG AGC CAT GAG CTC CTG CGG GAC TTC
Gly His Ala Gly Gly Arg Arg Ser Gly Gln Ser His Glu Leu Leu Arg Asp Phe 582                  597                  612          627
GAG GCG ACA CTT CTG CAG ATG TTT GGG CTG CGC CGC CCG CAG CCT AGC AAG
Glu Ala Thr Leu Leu Gln MET Phe Gly Leu Arg Arg Arg Pro Gln Pro Ser Lys 642                  657                  672
AGT GCC GTC ATT CCG GAC TAC ATG CGG GAT CTT TAC CGG CTT CAG TCT GGG GAG
Ser Ala Val Ile Pro Asp Tyr MET Arg Asp Leu Tyr Arg Leu Gln Ser Gly Glu 687                  702                  717          732
GAG GAA GAG CAG ATC CAC AGC ACT GGT CTT GAG TAT CCT GAG CGC CCG GCC
Glu Glu Glu Gln Ile His Ser Thr Gly Leu Glu Tyr Pro Glu Arg Pro Ala
```

Figure 2/3

```
                                          747                          762                          777
AGC CGG GCC AAC ACC GTG AGG AGC TTC CAC CAC GAA GAA CAT CTG GAG AAC ATC
Ser Arg Ala Asn Thr Val Arg Ser Phe His His Glu Glu His Leu Glu Asn Ile 792                          807                          822                          837
CCA GGG ACC AGT GAA AAC TCT GCT TTT CGT TTC CTC TTT AAC CTC AGC AGC ATC
Pro Gly Thr Ser Glu Asn Ser Ala Phe Arg Phe Leu Phe Asn Leu Ser Ser Ile 852                          867                          882                          897
CCT GAG AAC GAG GTG ATC TCC TCT GCA GAG CTT CGG GAG CTC TTC CGG GAG CAG GTG
Pro Glu Asn Glu Val Ile Ser Ser Ala Glu Leu Arg Glu Leu Phe Arg Glu Gln Val 912                          927                          942
GAC CAG GGC CCT GAT TGG GAA AGG GGC TTC CAC CGT ATA AAC ATT TAT GAG GTT
Asp Gln Gly Pro Asp Trp Glu Arg Gly Phe His Arg Ile Asn Ile Tyr Glu Val 957                          972                          987                         1002
ATG AAG CCC CCA GCA GAA GTG GTG CCT GGG CAC CTC ATC ACA CGA CTA CTG GAC
MET Lys Pro Pro Ala Glu Val Val Pro Gly His Leu Ile Thr Arg Leu Leu Asp
```

Figure 2/4

```
                    1017                       1032                        1047
ACG AGA CTG GTC CAC CAC AAT GTG ACA CGG TGG GAA ACT TTT GAT GTG AGC CCT
Thr Arg Leu Val His His Asn Val Thr Arg Trp Glu Thr Phe Asp Val Ser Pro 1062                       1077                       1092                       1107
GCG GTC CTT CGC TGG ACC CGG GAG AAG CAG CCA AAC TAT GGG CTA GCC ATT GAG
Ala Val Leu Arg Trp Thr Arg Glu Lys Gln Pro Asn Tyr Gly Leu Ala Ile Glu 1122                       1137                       1152                       1167
GTG ACT CAC CTC CAT CAG ACT CGG ACC CAC CAG GGC CAG CAT GTC AGG ATT AGC
Val Thr His Leu His Gln Thr Arg Thr His Gln Gly Gln His Val Arg Ile Ser 1182                       1197                       1212
CGA TCG TTA CCT CAA GGG AGT GGG AAT TGG GCC CAG CTC CGG CCC CTC CTG GTC
Arg Ser Leu Pro Gln Gly Ser Gly Asn Trp Ala Gln Leu Arg Pro Leu Leu Val 1227                       1242                       1257                       1272
ACC TTT GGC CAT GAT GGC CGG GGC CAT GCC TTG ACC CGA CGC CGG AGG GCC AAG
Thr Phe Gly His Asp Gly Arg Gly His Ala Leu Thr Arg Arg Arg Arg Ala Lys 1287                       1302                       1317
CGT AGC CCT AAG CAT CAC TCA CAG CGG GCC AGG AAG AAG AAT AAG AAC TGC CGG
Arg Ser Pro Lys His His Ser Gln Arg Ala Arg Lys Lys Asn Lys Asn Cys Arg
```

Figure 2/5

```
1332(311)                            1347                                   1362                                   1377
CGC CAC TCG CTC TAT GTG GAC TTC AGC GAT GTG GGC TGG AAT GAC TGG ATT GTG
Arg His Ser Leu Tyr Val Asp Phe Ser Asp Val Gly Trp Asn Asp Trp Ile Val 1392                                   1407                                   1422                   1437
GCC CCA CCA GGC TAC CAG GCC TTC TAC TGC CAT GGG GAC TGC CCC TTT CCA CTG
Ala Pro Pro Gly Tyr Gln Ala Phe Tyr Cys His Gly Asp Cys Pro Phe Pro Leu 1452                                   1467                   1482
GCT GAC CAC CTC AAC TCA ACC AAC CAT GCC ATT GTG CAG ACC CTG GTC AAT TCT
Ala Asp His Leu Asn Ser Thr Asn His Ala Ile Val Gln Thr Leu Val Asn Ser 1497                                   1512                                   1527                       1542
GTC AAT TCC AGT ATC CCC AAA GCC TGT TGT GTG CCC ACT GAA CTG AGT GCC ATC
Val Asn Ser Ser Ile Pro Lys Ala Cys Cys Val Pro Thr Glu Leu Ser Ala Ile 1557                                   1572                                   1587
TCC ATG CTG TAC CTG GAT GAG TAT GAT AAG GTG GTA CTG AAA AAT TAT CAG GAG
Ser MET Leu Tyr Leu Asp Glu Tyr Asp Lys Val Val Leu Lys Asn Tyr Gln Glu
```

Figure 2/6

```
1602                1617            (408)
ATG GTA GTA GAG GGA TGT GGG TGC CGC TGAGATCAGG CAGTCCTTGA GGATAGACAG
MET Val Val Glu Gly Cys Gly Cys Arg 1666       1676       1686       1696       1706       1716       1726
ATATACACAC CACACACACA CACCACATAC ACCACACACA CACGTTCCCA TCCACTCACC CACACACTAC 1736       1746       1756       1766       1776       1786       1796
ACAGACTGCT TCCTTATAGC TGGACTTTTA TTTAAAAAAA AAAAAAAAAA AATGGAAAAA ATCCCTAAAC 1806       1816       1826       1836       1846       1856       1866
ATTCACCTTG ACCTTATTTA TGACTTTACG TGCAAATGTT TTGACCATAT TGATCATATA TTTTGACAAA 1876       1886       1896       1906       1916       1926       1936
ATATATTTAT AACTACGTAT TAAAAGAAAA AAATAAAATG AGTCATTATT TTAAAAAAAA AAAAAAACT

1946
CTAGAGTCGA CGGAATTC
```

Figure 3

| | | | | | | | | | | | | | | | |
|---|---|---|---|---|---|---|---|---|---|---|---|---|---|---|---|
| TGA | ACA | AGA | GAG | TGC | TCA | AGA | AGC | TGT | CCA | AGG | ACG | GCT | CCA | CAG | AGG | 48
| * | Thr | Arg | Glu | Cys | Ser | Arg | Ser | Cys | Pro | Arg | Thr | Ala | Pro | Gln | Arg |
| -41 | -40 | | | | -35 | | | | | -30 | | | | | |

| CAG | GTG | AGA | GCA | GTC | ACG | AGG | AGG | ACA | CGG | ATG | GCG | CAC | GTG | GCT | GCG | 96
| Gln | Val | Arg | Ala | Val | Thr | Arg | Arg | Thr | Arg | Met | Ala | His | Val | Ala | Ala |
| -25 | | | | | -20 | | | | | -15 | | | | | -10 |

| GGG | TCG | ACT | TTA | GCC | AGG | CGG | AAA | AGG | AGC | GCC | GGG | GCT | GGC | AGC | CAC | 144
| Gly | Ser | Thr | Leu | Ala | Arg | Arg | Lys | Arg | Ser | Ala | Gly | Ala | Gly | Ser | His |
| | | | | -5 | | | | | 1 | | | | 5 | | |

| TGT | CAA | AAG | ACC | TCC | CTG | CGG | GTA | AAC | TTC | GAG | GAC | ATC | GGC | TGG | GAC | 192
| Cys | Gln | Lys | Thr | Ser | Leu | Arg | Val | Asn | Phe | Glu | Asp | Ile | Gly | Trp | Asp |
| | | 10 | | | | | 15 | | | | | 20 | | | |

| AGC | TGG | ATC | ATT | GCA | CCC | AAG | GAG | TAT | GAA | GCC | TAC | GAG | TGT | AAG | GGC | 240
| Ser | Trp | Ile | Ile | Ala | Pro | Lys | Glu | Tyr | Glu | Ala | Tyr | Glu | Cys | Lys | Gly |
| | 25 | | | | | 30 | | | | | 35 | | | | |

| GGC | TGC | TTC | TTC | CCC | TTG | GCT | GAC | GAT | GTG | ACG | CCG | ACG | AAA | CAC | GCT | 286
| Gly | Cys | Phe | Phe | Pro | Leu | Ala | Asp | Asp | Val | Thr | Pro | Thr | Lys | His | Ala |
| 40 | | | | | 45 | | | | | 50 | | | | | 55 |

| ATC | GTG | CAG | ACC | CTG | GTG | CAT | CTC | AAG | TTC | CCC | ACA | AAG | GTG | GGC | AAG | 336
| Ile | Val | Gln | Thr | Leu | Val | His | Leu | Lys | Phe | Pro | Thr | Lys | Val | Gly | Lys |
| | | | | 60 | | | | | 65 | | | | | 70 | |

| GCC | TGC | TGT | GTG | CCC | ACC | AAA | CTG | AGC | CCC | ATC | TCC | GTC | CTC | TAC | AAG | 384
| Ala | Cys | Cys | Val | Pro | Thr | Lys | Leu | Ser | Pro | Ile | Ser | Val | Leu | Tyr | Lys |
| | | | 75 | | | | | 80 | | | | | 85 | | |

| GAT | GAC | ATG | GGG | GTG | CCC | ACC | CTC | AAG | TAC | CAT | TAC | GAG | GGC | ATG | AGC | 432
| Asp | Asp | Met | Gly | Val | Pro | Thr | Leu | Lys | Tyr | His | Tyr | Glu | Gly | Met | Ser |
| | | | 90 | | | | | 95 | | | | | 100 | | |

| GTG | GCA | GAG | TGT | GGG | TGC | AGG | TAGTATCTGC | CTGCGGG | | | | | | | | 470
| Val | Ala | Glu | Cys | Gly | Cys | Arg | | | | | | | | | |
| | | | 105 | | | 110 | | | | | | | | | |

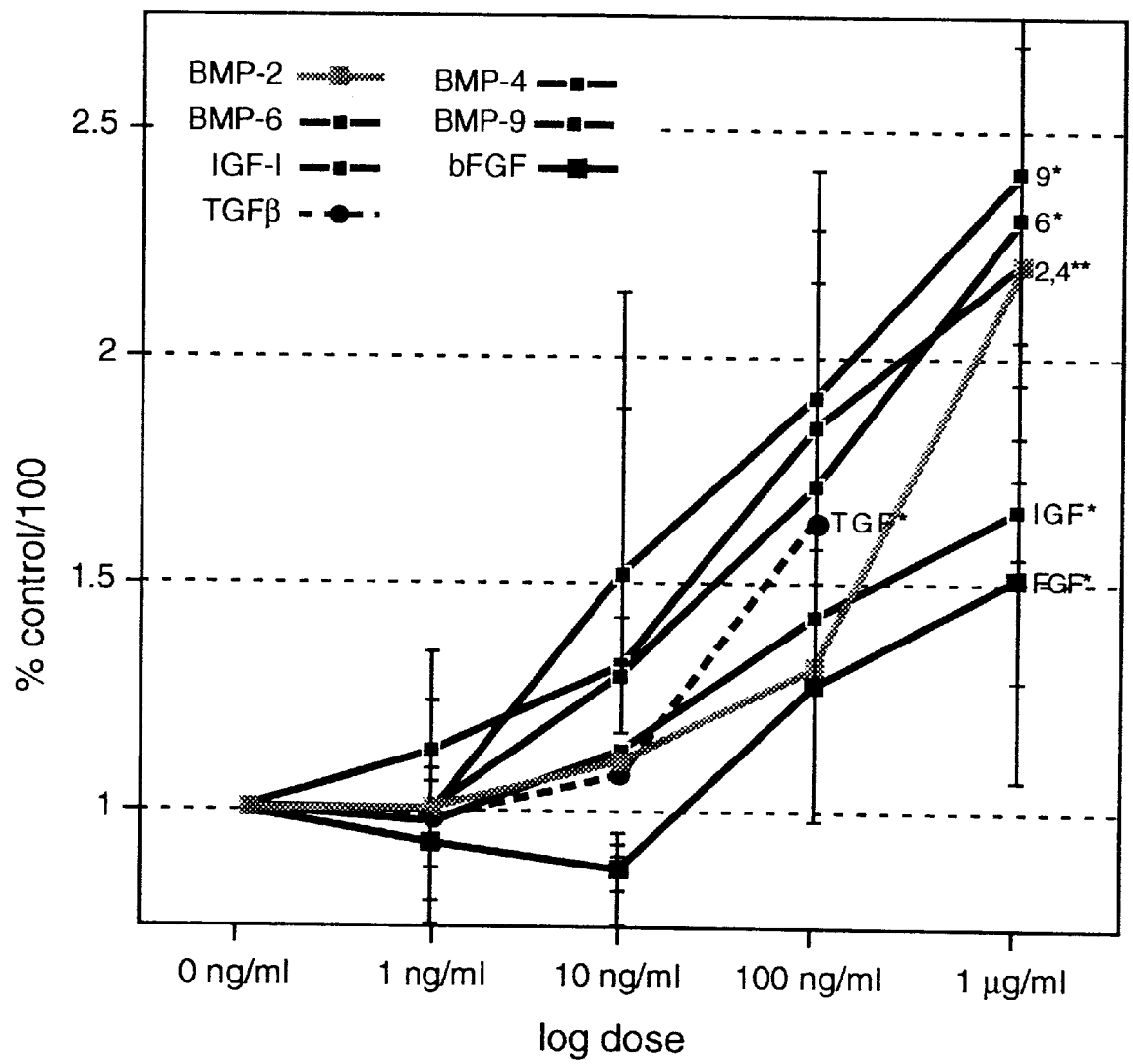

BMP-9 COMPOSITIONS

CROSS REFERENCE TO RELATED APPLICATIONS

This application is a continuation-in-part of U.S. Ser. No. 08/050,132 filed Apr. 22, 1993 now U.S. Pat. No. 5,661,007 which is a continuation-in-part of U.S. Ser. No. 07/720,590 filed Jun. 25, 1991, now abandoned.

The present invention relates to a novel family of purified proteins designated BMP-9 proteins and processes for obtaining them. These proteins may be used to induce bone and/or cartilage formation and in wound healing and tissue repair.

The murine BMP-9 DNA sequence (SEQ ID NO:1) and amino acid sequence (SEQ ID NO:2) are set forth in FIG. 1. Human BMP-9 sequence is set forth in FIG. 3 (SEQ ID NO:8 and SEQ ID NO:9). It is contemplated that BMP-9 proteins are capable of inducing the formation of cartilage and/or bone. BMP-9 proteins may be further characterized by the ability to demonstrate cartilage and/or bone formation activity in the rat bone formation assay described below.

Murine BMP-9 is characterized by comprising amino acid #319 to #428 of FIG. 1 (SEQ ID NO:2 amino acids #1–110). Murine BMP-9 may be produced by culturing a cell transformed with a DNA sequence comprising nucleotide #610 to nucleotide #1893 as shown in FIG. 1 (SEQ ID NO:1) and recovering and purifying from the culture medium a protein characterized by the amino acid sequence comprising amino acid #319 to #428 as shown in FIG. 1 (SEQ ID NO:2) substantially free from other proteinaceous materials with which it is co-produced.

Human BMP-9 is expected to be homologous to murine BMP-9 and is characterized by comprising amino acid #1 (Ser, Ala, Gly) to #110 of FIG. 3 (SEQ ID NO:9) (Arg). The invention includes methods for obtaining the DNA sequences encoding human BMP-9. This method entails utilizing the murine BMP-9 nucleotide sequence or portions thereof to design probes to screen libraries for the human gene or fragments thereof using standard techniques. Human BMP-9 may be produced by culturing a cell transformed with the BMP-9 DNA sequence and recovering and purifying BMP-9 from the culture medium. The expressed protein is isolated, recovered, and purified from the culture medium. The purified expressed protein is substantially free from other proteinaceous materials with which it is co-produced, as well as from other contaminants. The recovered purified protein is contemplated to exhibit cartilage and/or bone formation activity. The proteins of the invention may be further characterized by the ability to demonstrate cartilage and/or bone formation activity in the rat bone formation assay described below.

Human BMP-9 may be produced by culturing a cell transformed with a DNA sequence comprising nucleotide #124 to #453 as shown in SEQ ID NO:8 and recovering and purifying from the culture medium a protein characterized by the amino acid sequence of SEQ ID NO:9 from amino acid #1 to amino acid #110 substantially free from other proteinaceous materials with which it is co-produced.

Another aspect of the invention provides pharmaceutical compositions containing a therapeutically effective amount of a BMP-9 protein in a pharmaceutically acceptable vehicle or carrier. BMP-9 compositions of the invention may be used in the formation of cartilage. These compositions may further be utilized for the formation of bone. BMP-9 compositions may also be used for wound healing and tissue repair. Compositions of the invention may further include at least one other therapeutically useful agent such as the BMP proteins BMP-1, BMP-2, BMP-3, BMP-4, BMP-5, BMP-6, and BMP-7 disclosed for instance in PCT Publication Nos. WO88/00205, WO89/10409, and WO90/11366, and BMP-8, disclosed in U.S. application Ser. No. 07/641,204 filed Jan. 15, 1991, now abandoned Ser. No. 07/525,357 filed May 16, 1990, now abandoned and Ser. No. 07/800,364, U.S. Pat. No. 5,688,678, filed Nov. 20, 1991.

The compositions of the invention may comprise, in addition to a BMP-9 protein, other therapeutically useful agents including growth factors such as epidermal growth factor (EGF), fibroblast growth factor (FGF), transforming growth factor (TGF-α and TGF-β), and insulin-like growth factor (IGF). The compositions may also include an appropriate matrix for instance, for supporting the composition and providing a surface for bone and/or cartilage growth. The matrix may provide slow release of the osteoinductive protein and/or the appropriate environment for presentation thereof.

The BMP-9 compositions may be employed in methods for treating a number of bone and/or cartilage defects, periodontal disease and various types of wounds. These methods, according to the invention, entail administering to a patient needing such bone and/or cartilage formation wound healing or tissue repair, an effective amount of a BMP-9 protein. These methods may also entail the administration of a protein of the invention in conjunction with at least one of the novel BMP proteins disclosed in the co-owned applications described above. In addition, these methods may also include the administration of a BMP-9 protein with other growth factors including EGF, FGF, TGF-α, TGF-β, and IGF.

Still a further aspect of the invention are DNA sequences coding for expression of a BMP-9 protein. Such sequences include the sequence of nucleotides in a 5' to 3' direction illustrated in FIG. 1 (SEQ ID NO:1) and FIG. 3 (SEQ ID NO:8) or DNA sequences which hybridize under stringent conditions with the DNA sequences of FIG. 1 or 3 and encode a protein having the ability to induce the formation of cartilage and/or bone. Finally, allelic or other variations of the sequences of FIG. 1 or 3, whether such nucleotide changes result in changes in the peptide sequence or not, are also included in the present invention.

A further aspect of the invention includes vectors comprising a DNA sequence as described above in operative association with an expression control sequence therefor. These vectors may be employed in a novel process for producing a BMP-9 protein of the invention in which a cell line transformed with a DNA sequence encoding a BMP-9 protein in operative association with an expression control sequence therefor, is cultured in a suitable culture medium and a BMP-9 protein is recovered and purified therefrom. This process may employ a number of known cells both prokaryotic and eukaryotic as host cells for expression of the polypeptide.

Other aspects and advantages of the present invention will be apparent upon consideration of the following detailed description and preferred embodiments thereof.

BRIEF DESCRIPTION OF THE DRAWINGS

FIGS. 1/1 through 1/8 comprises DNA sequence and derived amino acid sequence of murine BMP-9 from clone ML14a further described below (SEQ ID NO:1 and 2).

FIGS. 2/1 through 2/6 comprises DNA sequence and derived amino acid sequence of human BMP-4 from lambda U2OS-3 ATCC #40342 (SEQ ID NO:3 and 4).

FIG. 3 comprises DNA sequence and derived amino acid sequence of human BMP-9 from λ FIX/H6111 ATCC #75252 (SEQ ID NO:8 and 9).

FIG. 4 sets forth sulfate incorporation results of BMP-9 and other proteins added to bovine articular cartilage explants.

DETAILED DESCRIPTION OF THE INVENTION

The murine BMP-9 nucleotide sequence (SEQ ID NO:1) and encoded amino acid sequence (SEQ ID NO:2) are depicted in FIG. 1. Purified murine BMP-9 proteins of the present invention are produced by culturing a host cell transformed with a DNA sequence comprising the DNA coding sequence of FIG. 1 (SEQ ID NO:1) from nucleotide #610 to nucleotide #1893 and recovering and purifying from the culture medium a protein which contains the amino acid sequence or a substantially homologous sequence as represented by amino acid #319 to #428 of FIG. 1 (SEQ ID NO:2). The BMP-9 proteins recovered from the culture medium are purified by isolating them from other proteinaceous materials from which they are co-produced and from other contaminants present.

Human BMP-9 nucleotide and amino acid sequence is depicted in SEQ ID No: 8 and 9. Mature human BMP-9 is expected to comprise amino acid #1 (Ser, Ala, Gly) to #110 (Arg).

Human BMP-9 may be produced by culturing a cell transformed with a DNA sequence comprising nucleotide #124 to #453 as shown in SEQ ID NO:8 and recovering and purifying from the culture medium a protein characterized by the amino acid sequence of SEQ ID NO:9 from amino acid #1 to amino acid #110 substantially free from other proteinaceous materials with which it is co-produced.

BMP-9 proteins may be characterized by the ability to induce the formation of cartilage. BMP-9 proteins may be further characterized by the ability to induce the formation of bone. BMP-9 proteins may be further characterized by the ability to demonstrate cartilage and/or bone formation activity in the rat bone formation assay described below.

The BMP-9 proteins provided herein also include factors encoded by the sequences similar to those of FIGS. 1 and 3 (SEQ ID NOS:1 and 8), but into which modifications are naturally provided (e.g., allelic variations in the nucleotide sequence which may result in amino acid changes in the polypeptide) or deliberately engineered. For example, synthetic polypeptides may wholly or partially duplicate continuous sequences of the amino acid residues of FIG. 1 of FIG. 3 (SEQ ID NOS:2 and 9). These sequences, by virtue of sharing primary, secondary, or tertiary structural and conformational characteristics with bone growth factor polypeptides of FIG. 1 and FIG. 3 may possess bone growth factor biological properties in common therewith. Thus, they may be employed as biologically active substitutes for naturally-occurring BMP-9 and other BMP-9 polypeptides in therapeutic processes.

Other specific mutations of the sequences of BMP-9 proteins described herein involve modifications of glycosylation sites. These modifications may involve O-linked or N-linked glycosylation sites. For instance, the absence of glycosylation or only partial glycosylation results from amino acid substitution or deletion at asparagine-linked glycosylation recognition sites. The asparagine-linked glycosylation recognition sites comprise tripeptide sequences which are specifically recognized by appropriate cellular glycosylation enzymes. These tripeptide sequences are either asparagine-X-threonine or asparagine-X-serine, where X is usually any amino acid. A variety of amino acid substitutions or deletions at one or both of the first or third amino acid positions of a glycosylation recognition site (and/or amino acid deletion at the second position) results in non-glycosylation at the modified tripeptide sequence.

The present invention also encompasses the novel DNA sequences, free of association with DNA sequences encoding other proteinaceous materials, and coding on expression for BMP-9 proteins. These DNA sequences include those depicted in FIG. 1 or FIG. 3 (SEQ ID NOS:1 and 8) in a 5' to 3' direction and those sequences which hybridize thereto under stringent hybridization conditions [see, T. Maniatis et al., *Molecular Cloning (A Laboratory Manual)*, Cold Spring Harbor Laboratory (1982), pages 387 to 389] and encode a protein having cartilage and/or bone inducing activity.

Similarly, DNA sequences which code for BMP-9 proteins coded for by the sequences of FIG. 1 or FIG. 3, but which differ in codon sequence due to the degeneracies of the genetic code or allelic variations (naturally-occurring base changes in the species population which may or may not result in an amino acid change) also encode the novel factors described herein. Variations in the DNA sequences of FIG. 1 or FIG. 3 (SEQ ID NOS:1 and 8) which are caused by point mutations or by induced modifications (including insertion, deletion, and substitution) to enhance the activity, half-life or production of the polypeptides encoded are also encompassed in the invention.

Another aspect of the present invention provides a novel method for producing BMP-9 proteins. The method of the present invention involves culturing a suitable cell line, which has been transformed with a DNA sequence encoding a BMP-9 protein of the invention, under the control of known regulatory sequences. The transformed host cells are cultured and the BMP-9 proteins recovered and purified from the culture medium. The purified proteins are substantially free from other proteins with which they are co-produced as well as from other contaminants.

Suitable cells or cell lines may be mammalian cells, such as Chinese hamster ovary cells (CHO). The selection of suitable mammalian host cells and methods for transformation, culture, amplification, screening, product production and purification are known in the art. See e.g., Gething and Sambrook, Nature 293:620–625 (1981), or alternatively, Kaufman et al., Mol. Cell. Biol. 5(7) :1750–1759 (1985) or Howley et al., U.S. Pat. No. 4,419, 446. Another suitable mammalian cell line, which is described in the accompanying examples, is the monkey COS-1 cell line. The mammalian cell CV-1 may also be suitable.

Bacterial cells may also be suitable hosts. For example, the various strains of *E. coli* (e.g., HB101, MC1061) are well-known as host cells in the field of biotechnology. Various strains of *B. subtilis*, Pseudomonas, other bacilli and the like may also be employed in this method.

Many strains of yeast cells known to those skilled in the art may also be available as host cells for expression of the polypeptides of the present invention. Additionally, where desired, insect cells may be utilized as host cells in the method of the present invention. See e.g., Miller et al., Genetic Engineering 8:277–298 (Plenum Press 1986) and references cited therein.

Another aspect of the present invention provides vectors for use in the method of expression of these novel BMP-9 polypeptides. Preferably the vectors contain the full novel DNA sequences described above which encode the novel factors of the invention. Additionally the vectors also contain appropriate expression control sequences permitting expression of the BMP-9 protein sequences. Alternatively, vectors incorporating modified sequences as described above are also embodiments of the present invention. The vectors may be employed in the method of transforming cell lines and contain selected regulatory sequences in operative association with the DNA coding sequences of the invention which are capable of directing the replication and expression thereof in selected host cells. Regulatory sequences for such vectors are known to those skilled in the art and may be selected depending upon the host cells. Such selection is routine and does not form part of the present invention.

A protein of the present invention, which induces cartilage and/or bone formation in circumstances where bone is not normally formed, has application in the healing of bone fractures and cartilage defects in humans and other animals. Such a preparation employing a BMP-9 protein may have prophylactic use in closed as well as open fracture reduction and also in the improved fixation of artificial joints. De novo bone formation induced by an osteogenic agent contributes to the repair of congenital, trauma induced, or oncologic resection induced craniofacial defects, and also is useful in cosmetic plastic surgery. A BMP-9 protein may be used in the treatment of periodontal disease, and in other tooth repair processes. Such agents may provide an environment to attract bone-forming cells, stimulate growth of bone-forming cells or induce differentiation of progenitors of bone-forming cells. BMP-9 polypeptides of the invention may also be useful in the treatment of osteoporosis. BMP-9 may be used in cartilage defect repair and prevention/reversal of osteoarthritis. A variety of osteogenic, cartilage-inducing and bone inducing factors have been described. See e.g., European Patent Application Nos. 148,155 and 169,016 for discussions thereof.

The proteins of the invention may also be used in wound healing and related tissue repair. The types of wounds include, but are not limited to burns, incisions and ulcers. (See e.g., PCT Publication No. WO84/01106 for discussion of wound healing and related tissue repair).

It is further contemplated that proteins of the invention may increase neuronal survival and therefore be useful in transplantation and treatment of conditions exhibiting a decrease in neuronal survival.

A further aspect of the invention is a therapeutic method and composition for repairing fractures and other conditions related to cartilage and/or bone defects or periodontal diseases. The invention further comprises therapeutic methods and compositions for wound healing and tissue repair. Such compositions comprise a therapeutically effective amount of at least one of the BMP-9 proteins of the invention in admixture with a pharmaceutically acceptable vehicle, carrier or matrix. It is expected that the proteins of the invention may act in concert with or perhaps synergistically with other related proteins and growth factors. Further therapeutic methods and compositions of the invention therefore comprise a therapeutic amount of at least one BMP-9 protein of the invention with a therapeutic amount of at least one of the other BMP proteins disclosed in co-owned applications described above. Such combinations may comprise separate molecules of the BMP proteins or heteromolecules comprised of different BMP moieties. For example, a method and composition of the invention may comprise a disulfide linked dimer comprising a BMP-9 protein subunit and a subunit from one of the "BMP" proteins described above. A further embodiment may comprise a heterodimer of BMP-9 moieties. Further, BMP-9 proteins may be combined with other agents beneficial to the treatment of the bone and/or cartilage defect, wound, or tissue in question. These agents include various growth factors such as epidermal growth factor (EGF), platelet derived growth factor (PDGF), transforming growth factors (TGF-$\alpha$ and TGF-$\beta$), and insulin-like growth factor (IGF).

The preparation and formulation of such physiologically acceptable protein compositions, having due regard to pH, isotonicity, stability and the like, is within the skill of the art. The therapeutic compositions are also presently valuable for veterinary applications due to the lack of species specificity in BMP proteins. Particularly domestic animals and thoroughbred horses in addition to humans are desired patients for such treatment with BMP-9 of the present invention.

The therapeutic method includes administering the composition topically, systemically, or locally as an implant or device. When administered, the therapeutic composition for use in this invention is, of course, in a pyrogen-free, physiologically acceptable form. Further, the composition may desirably be encapsulated or injected in a viscous form for delivery to the site of bone, cartilage or tissue damage. Topical administration may be suitable for wound healing and tissue repair. Therapeutically useful agents other than the BMP-9 proteins which may also optionally be included in the composition as described above, may alternatively or additionally, be administered simultaneously or sequentially with the BMP composition in the methods of the invention. Preferably for bone and/or cartilage formation, the composition would include a matrix capable of delivering BMP-9 or other BMP proteins to the site of bone and/or cartilage damage, providing a structure for the developing bone and cartilage and optimally capable of being resorbed into the body. The matrix may provide slow release of BMP-9 and/or the appropriate environment for presentation thereof. Such matrices may be formed of materials presently in use for other implanted medical applications.

The choice of matrix material is based on biocompatibility, biodegradability, mechanical properties, cosmetic appearance and interface properties. The particular application of the BMP-9 compositions will define the appropriate formulation. Potential matrices for the compositions may be biodegradable and chemically defined calcium sulfate, tricalciumphosphate, hydroxyapatite, polylactic acid and polyanhydrides. Other potential materials are biodegradable and biologically well defined, such as bone or dermal collagen. Further matrices are comprised of pure proteins or extracellular matrix components. Other potential matrices are nonbiodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalciumphosphate. The bioceramics may be altered in composition, such as in calcium-aluminate-phosphate and processing to alter pore size, particle size, particle shape, and biodegradability.

The dosage regimen will be determined by the attending physician considering various factors which modify the action of the BMP-9 protein, e.g., amount of bone weight desired to be formed, the site of bone damage, the condition of the damaged bone, the size of a wound, type of damaged tissue, the patient's age, sex, and diet, the severity of any infection, time of administration and other clinical factors. The dosage may vary with the type of matrix used in the reconstitution and the types of BMP proteins in the composition. The addition of other known growth factors, such as IGF I (insulin like growth factor I), to the final composition, may also effect the dosage. Progress can be monitored by periodic assessment of bone growth and/or repair, for example, x-rays, histomorphometric determinations and tetracycline labeling.

The following examples illustrate practice of the present invention in recovering and characterizing murine BMP-9 protein and employing it to recover the human and other BMP-9 proteins, obtaining the human proteins and expressing the proteins via recombinant techniques.

EXAMPLE I
Murine BMP-9

750,000 recombinants of a mouse liver cDNA library made in the vector lambdaZAP (Stratagene/Catalog #935302) are plated and duplicate nitrocellulose replicas made. A fragment of human BMP-4 DNA corresponding to nucleotides 1330–1627 of FIG. 2 (SEQ ID NO:3) (the human BMP-4 sequence) is $^{32}$P-labeled by the random priming procedure of Feinberg et al., Anal. Biochem. 132:6–13 (1983) and hybridized to both sets of filters in SHB at 60° C. for 2 to 3 days. Both sets of filters are washed under reduced stringency conditions (4xSSC, 0.1% SDS at 60° C.). Many duplicate hybridizing recombinants of various intensities (approximately 92) are noted. 50 of the strongest hybridizing recombinant bacteriophage are plaque purified and their inserts are transferred to the plasmid Bluescript SK (+/−) according to the in vivo excision protocol described by the manufacturer (Stratagene). DNA sequence analysis of several recombinants indicate that they encode a protein homologous to other BMP proteins and other proteins in the TGF-β family. The DNA sequence and derived amino acid sequence of one recombinant, designated ML14a, is set forth in FIG. 1. (SEQ ID NO:1).

The nucleotide sequence of clone ML14a contains an open reading frame of 1284 bp, encoding a BMP-9 protein of 428 amino acids. The encoded 428 amino acid BMP-9 protein is contemplated to be the primary translation product as the coding sequence is preceded by 609 bp of 5' untranslated sequence with stop codons in all three reading frames. The 428 amino acid sequence predicts a BMP-9 protein with a molecular weight of 48,000 daltons.

Based on knowledge of other BMP proteins and other proteins within the TGF-β family, it is predicted that the precursor polypeptide would be cleaved at the multibasic sequence ARG-ARG-LYS-ARG amino acids #-4 to #-1 of SEQ ID NO:1 in agreement with a proposed consensus proteolytic processing sequence of ARG-X-X-ARG amino acids #-4 to #-1 of SEQ ID NO: 1. Cleavage of the BMP-9 precursor polypeptide at this location would generate a 110 amino acid mature peptide beginning with the amino acid SER at position #319 of FIG. 1C and amino acid #1 of SEQ ID NO:2. The processing of BMP-9 into the mature form is expected to involve dimerization and removal of the N-terminal region in a manner analogous to the processing of the related protein TGF-β [L. E. Gentry et al., Mol. & Cell. Biol. 8:4162 (1988); R. Derynck et al., Nature 316:701 (1985)].

It is contemplated therefore that the mature active species of murine BMP-9 comprises a homodimer of 2 polypeptide subunits, each subunit comprising amino acids #319–#428 of FIG 1C and amino acid #1–#110 of SEQ ID NO:2 with a predicted molecular weight of approximately 12,000 daltons. Further active species are contemplated comprising amino acids #326–#428 of FIG. 1C and amino acid #8–#110 of SEQ ID NO:2 thereby including the first conserved cysteine residue. As with other members of the BMP and TGF-β family of proteins, the carboxy-terminal region of the BMP-9 protein exhibits greater sequence conservation than the more amino-terminal portion. The percent amino acid identity of the murine BMP-9 protein in the cysteine-rich C-terminal domain (amino acids #326–#428 of FIG. 1C and amino acid #8–#110 of SEQ ID NO:2) to the corresponding region of other human BMP proteins and other proteins within the TGF-β family is as follows: BMP-2, 53%; BMP-3, 43%; BMP-4, 53%; BMP-5, 55%; BMP-6, 55%; BMP-7, 53%; Vgl, 50%; GDF-1, 43%; TGF-β1, 32%; TGF-β2, 34%; TGF-β3, 34%; inhibin β(B), 34%; and inhibin β(A), 42%.

EXAMPLE II
Human BMP-9

Murine and human osteoinductive factor genes are presumed to be significantly homologous, therefore the murine coding sequence or a portion thereof is used as a probe to screen a human genomic library or as a probe to identify a human cell line or tissue which synthesizes the analogous human cartilage and/or bone protein. A human genomic library (Toole et al., supra) may be screened with such a probe, and presumptive positives isolated and DNA sequence obtained. Evidence that this recombinant encodes a portion of the human BMP-9 relies of the murine/human protein and gene structure homologies.

Once a recombinant bacteriophage containing DNA encoding portion of the human cartilage and/or bone inductive factor molecule is obtained, the human coding sequence can be used as a probe to identify a human cell line or tissue which synthesizes BMP-9. Alternatively, the murine coding sequence can be used as a probe to identify such human cell line or tissue. Briefly described, RNA is extracted from a selected cell or tissue source and either electrophoresed on a formaldehyde agarose gel and transferred to nitrocellulose, or reacted with formaldehyde and spotted on nitrocellulose directly. The nitrocellulose is then hybridized to a probe derived from a coding sequence of the murine or human BMP-9. mRNA is selected by oligo (dT) cellulose chromatography and cDNA is synthesized and cloned in lambda gt10 or lambda ZAP by established techniques (Toole et al., supra).

Additional methods known to those skilled in the art may be used to isolate the human and other species' BMP-9 proteins of the invention.

A. Isolation of Human BMP-9 DNA

One million recombinants of a human genomic library constructed in the vector λFIX (Stratagene catalog #944201) are plated and duplicate nitrocellulose replicas made. Two oligonucleotides probes designed on the basis of nucleotides #1665–#1704 and #1837–#1876 of the sequence set forth in FIG. 1 (SEQ ID NO:1) are synthesized on an automated DNA synthesizer. The sequence of these two oligonucleotides is indicated below:

1: CTATGAGTGTAAAGGGGGTTGCTTCTTC-CCATTGGCTGAT

2: GTGCCAACCCTCAAGTACCACTAT-GAGGGGATGAGTGTGG

These two oligonucleotide probes are radioactively labeled with $\gamma^{32}$P-ATP and each is hybridized to one set of the duplicate nitrocellulose replicas in SHB at 65° C. and washed with 1xSSC, 0.1% SDS at 65° C. Three recombinants which hybridize to both oligonucleotide probes are noted. All three positively hybridizing recombinants are plaque purified, bacteriophage plate stocks are prepared and bacteriophage DNA is isolated from each. The oligonucleotide hybridizing regions of one of these recombinants, designated HG111, is localized to a 1.2 kb Pst I/Xba I fragment. This fragment is subcloned into a plasmid vector (pGEM-3) and DNA sequence analysis is performed. HG111 was deposited with the American Type Culture Collection ATCC, 12301 Parklawn Drive, Rockville, Md. USA on Jun. 16, 1992 under the requirements of the Budapest Treaty and designated as ATCC #75252. This subclone is designated pGEM-111. A portion of the DNA sequence of clone pGEM-111 is set forth in FIG. 3 (SEQ ID NO:8/ HUMAN BMP-9 SEQUENCE). This sequence encodes the entire mature region of human BMP-9 and a portion of the propeptide. It should be noted that this sequence consists of preliminary data. Particularly, the propeptide region is subject to further analysis and characterization. For example, nucleotides #1 through #3 (TGA) (SEQ ID NO:8) encode a translational stop which may be incorrect due to the preliminary nature of the sequence. It is predicted that additional sequences present in both pGEM-111 (the 1.2 kb PstI/XbaI fragment of HG111 subcloned into pGEM) and HG111 encode additional amino acids of the human BMP-9 propeptide region. Based on knowledge of other BMPs and other proteins within the TGF-β family, it is predicted that the precursor polypeptide would be cleaved at the multibasic sequence ARG-ARG-LYS-ARG (amino acids #-4 through #-1 of SEQ ID NO:9) in agreement with a proposed consensus proteolytic processing sequence ARG-X-X-ARG amino acids #-4 through -1 SEQ ID NO: 9. Cleavage of the human BMP-9 precursor polypeptide at this location would generate a 110 amino acid mature peptide beginning with the amino acid SER at position #1 of SEQ ID NO:9 (encoded by nucleotides #124 through #126 of SEQ ID NO:8). The processing of human BMP-9 into the mature form is expected to involve dimerization and removal of the N-terminal region in a manner analogous to the processing of the related protein TGF-β [L. E. Gentry et al., Mol. & Cell. Biol. 8:4162 (1988); R. Derynck et al., Nature 316:701 (1985)].

It is contemplated therefore that the mature active species of human BMP-9 comprises a homodimer of two polypeptide subunits, each subunit comprising amino acids #1 through #110 of SEQ ID NO:9, with a predicted molecular weight of 12,000 daltons. Further active species are contemplated comprising amino acids #8 through #110 (SEQ ID NO:9) thereby including the first conserved cysteine residue. As with other members of the BMP and TGF-β family of proteins, the carboxy-terminal portion of the human BMP-9 sequence exhibits greater sequence conservation than the amino-terminal portion. The percent amino acid identity of the human BMP-9 protein in the cysteine-rich C-terminal domain (amino acids #8 through #110) to the corresponding region of other human BMP proteins and other proteins within the TGF-β family is as follows: BMP-2, 52%; BMP-3, 40%; BMP-4, 52%; BMP-5, 55%; BMP-6, 55%; BMP-7, 53%; murine BMP-9, 97%; Vg1, 50%; GDF-1, 44%; TGF-β1, 32%; TGF-β2, 32%; TGF-β3, 32%; inhibin β (B), 35%; and inhibin β (A), 41%. BMP-9 exhibits 80% homology to chick Dorsalin-1, a BMP-like protein cloned from embryonic chick.

EXAMPLE III
Rosen Modified Sampath-Reddi Assay

A modified version of the rat bone formation assay described in Sampath and Reddi, Proc. Natl. Acad. Sci. USA 80:6591–6595 (1983) is used to evaluate bone and/or cartilage activity of the BMP proteins. This modified assay is herein called the Rosen-modified Sampath-Reddi assay. The ethanol precipitation step of the Sampath-Reddi procedure is replaced by dialyzing (if the composition is a solution) or diafiltering (if the composition is a suspension) the fraction to be assayed against water. The solution or suspension is then redissolved in 0.1% TFA, and the resulting solution added to 20 mg of rat matrix. A mock rat matrix sample not treated with the protein serves as a control. This material is frozen and lyophilized and the resulting powder enclosed in #5 gelatin capsules. The capsules are implanted subcutaneously in the abdominal thoracic area of 21–49 day old male Long Evans rats. The implants are removed after 7–14 days. Half of each implant is used for alkaline phosphatase analysis [See, A. H. Reddi et al., Proc. Natl Acad Sci. 69:1601 (1972)].

The other half of each implant is fixed and processed for histological analysis. 1 lm glycolmethacrylate sections are stained with Von Kossa and acid fuschin to score the amount of induced bone and cartilage formation present in each implant. The terms +1 through +5 represent the area of each histological section of an implant occupied by new bone and/or cartilage cells and matrix. A score of +5 indicates that greater than 50% of the implant is new bone and/or cartilage produced as a direct result of protein in the implant. A score of +4, +3, +2 and +1 would indicate that greater than 40%, 30%, 20% and 10% respectively of the implant contains new cartilage and/or bone. In a modified scoring method, three non-adjacent sections are evaluated from each implant and averaged. "+/−" indicates tentative identification of cartilage or bone; "+1" indicates >10% of each section being new cartilage or bone; "+2", >25%; "+3", >50%; "+4", ~75%; "+5", >80%. A "−" indicates that the implant is not recovered.

It is contemplated that the dose response nature of the BMP-9 containing samples of the matrix samples will demonstrate that the amount of bone and/or cartilage formed increases with the amount of BMP-9 in the sample. It is contemplated that the control samples will not result in any bone and/or cartilage formation.

As with other cartilage and/or bone inductive proteins such as the above-mentioned "BMP" proteins, the bone and/or cartilage formed is expected to be physically confined to the space occupied by the matrix. Samples are also analyzed by SDS gel electrophoresis and isoelectric focusing followed by autoradiography. The activity is correlated with the protein bands and pI. To estimate the purity of the protein in a particular fraction an extinction coefficient of 1 OD/mg-cm is used as an estimate for protein and the protein is run on SDS PAGE followed by silver staining or radio-iodination and autoradiography.

EXAMPLE IV
Expression of BMP-9

In order to produce murine, human or other mammalian BMP-9 proteins, the DNA encoding it is transferred into an appropriate expression vector and introduced into mammalian cells or other preferred eukaryotic or prokaryotic hosts by conventional genetic engineering techniques. The preferred expression system for biologically active recombinant human BMP-9 is contemplated to be stably transformed mammalian cells.

One skilled in the art can construct mammalian expression vectors by employing the sequence of FIG. 1 (SEQ ID NO:1) or FIG. 3 (SEQ ID NO:8), or other DNA sequences encoding BMP-9 proteins or other modified sequences and known vectors, such as pCD [Okayama et al., Mol. Cell Biol. 2:161–170 (1982)], pJL3, pJL4 [Gough et al., EMBO J. 4:645–653 (1985)] and pMT2 CXM.

The mammalian expression vector pMT2 CXM is a derivative of p91023 (b) (Wong et al., Science 228:810–815 (1985)) differing from the latter in that it contains the ampicillin resistance gene in place of the tetracycline resistance gene and further contains a XhoI site for insertion of cDNA clones. The functional elements of pMT2 CXM have been described (Kaufman, R. J., Proc. Natl. Acad. Sci. USA 82:689–693 (1985)) and include the adenovirus VA genes, the SV40 origin of replication including the 72 bp enhancer, the adenovirus major late promoter including a 5' splice site and the majority of the adenovirus tripartite leader sequence present on adenovirus late mRNAs, a 3' splice acceptor site, a DHFR insert, the SV40 early polyadenylation site (SV40), and pBR322 sequences needed for propagation in E. coli.

Plasmid pMT2 CXM is obtained by EcoRI digestion of pMT2-VWF, which has been deposited with the American Type Culture Collection (ATCC), Rockville, Md. (USA) under accession number ATCC #67122. EcoRI digestion excises the cDNA insert present in pMT2-VWF, yielding pMT2 in linear form which can be ligated and used to transform E. coli HB 101 or DH-5 to ampicillin resistance. Plasmid pMT2 DNA can be prepared by conventional methods. pMT2 CXM is then constructed using loopout/in mutagenesis [Morinaga et al., Biotechnology 84:636 (1984)]. This removes bases 1075 to 1145 relative to the Hind III site near the SV40 origin of replication and enhancer sequences of pMT2. In addition it inserts the following sequence:

5' PO-CATGGGCAGCTCGAG-3' (SEQ ID NO:5)

at nucleotide 1145. This sequence contains the recognition site for the restriction endonuclease Xho I. A derivative of pMT2CXM, termed pMT23, contains recognition sites for the restriction endonucleases PstI, Eco RI, SalI and XhoI. Plasmid pMT2 CXM and pMT23 DNA may be prepared by conventional methods. pEMC2b1 derived from pMT21 may also be suitable in practice of the invention. pMT21 is derived from pMT2 which is derived from pMT2-VWF. As described above EcoRI digestion excises the cDNA insert present in pMT-VWF, yielding pMT2 in linear form which can be ligated and used to transform E. coli HB 101 or DH-5 to ampicillin resistance. Plasmid pMT2 DNA can be prepared by conventional methods.

pMT21 is derived from pMT2 through the following two modifications. First, 76 bp of the 5' untranslated region of the DHFR cDNA including a stretch of 19 G residues from G/C tailing for cDNA cloning is deleted. In this process, a XhoI site is inserted to obtain the following sequence immediately upstream from DHFR:

```
                                    (SEQ ID NO:6)
5'-CTGCAGGCGAGCCTGAATTCCTCGAGCCATCATG-3' (SEQ
                                         ID
                                         NO:6)
          PstI           Eco RI  XhoI
```

Second, a unique ClaI site is introduced by digestion with EcoRV and XbaI, treatment with Klenow fragment of DNA polymerase I, and ligation to a ClaI linker (CATCGATG). This deletes a 250 bp segment from the adenovirus associated RNA (VAI) region but does not interfere with VAI RNA gene expression or function. pMT21 is digested with EcoRI and XhoI, and used to derive the vector pEMC2B1.

A portion of the EMCV leader is obtained from pMT2-ECAT1 [S.K. Jung et al., J. Virol 63:1651–1660 (1989)] by digestion with Eco RI and PstI, resulting in a 2752 bp fragment. This fragment is digested with TaqI yielding an Eco RI-TaqI fragment of 508 bp which is purified by electrophoresis on low melting agarose gel. A 68 bp adapter and its complementary strand are synthesized with a 5' TaqI protruding end and a 3' XhoI protruding end which has the following sequence:

```
5'-CGAGGTTAAAAAACGTCTAGGCCCCCCGAACCACGGGGACGTGGTTTTCCTTT   (SEQ ID NO:7)
   TaqI

GAAAAACACGATTGC-3'
                         XhoI
```

This sequence matches the EMC virus leader sequence from nucleotide 763 to 827. It also changes the ATG at position 10 within the EMC virus leader to an ATT and is followed by a XhoI site. A three way ligation of the pMT21 Eco RI-XhoI fragment, the EMC virus EcoRI-TaqI fragment, and the 68 bp oligonucleotide adapter TaqI-XhoI adapter resulting in the vector pEMC2β1.

This vector contains the SV40 origin of replication and enhancer, the adenovirus major late promoter, a cDNA copy of the majority of the adenovirus tripartite leader sequence, a small hybrid intervening sequence, an SV40 polyadenylation signal and the adenovirus VA I gene, DHFR and β-lactamase markers and an EMC sequence, in appropriate relationships to direct the high level expression of the desired cDNA in mammalian cells.

The construction of vectors may involve modification of the BMP-9 DNA sequences. For instance, BMP-9 cDNA can be modified by removing the non-coding nucleotides on the 5' and 3' ends of the coding region. The deleted non-coding nucleotides may or may not be replaced by other sequences known to be beneficial for expression. These vectors are transformed into appropriate host cells for expression of BMP-9 proteins. One skilled in the art can manipulate the sequences of FIG. 1 or FIG. 3 (SEQ ID NOS:1 and 8) by eliminating or replacing the mammalian regulatory sequences flanking the coding sequence with bacterial sequences to create bacterial vectors for intracellular or extracellular expression by bacterial cells. For example, the coding sequences could be further manipulated (e.g., ligated to other known linkers or modified by deleting non-coding sequences therefrom or altering nucleotides therein by other known techniques). The modified BMP-9 coding sequence could then be inserted into a known bacterial vector using procedures such as described in T. Taniguchi et al., Proc. Natl Acad. Sci. USA 77:5230–5233 (1980). This exemplary bacterial vector could then be transformed into bacterial host cells and a BMP-9 protein expressed thereby. For a strategy for producing extracellular expression of BMP-9 proteins in bacterial cells, see e.g., European Patent Application No. EPA 177,343.

Similar manipulations can be performed for the construction of an insect vector [See e.g., procedures described in published European Patent Application No. 155,476] for expression in insect cells. A yeast vector could also be constructed employing yeast regulatory sequences for intracellular or extracellular expression of the factors of the present invention by yeast cells. [See e.g., procedures described in published PCT Publication No. WO86/00639 and European Patent Application No. EPA 123,289].

A method for producing high levels of a BMP-9 protein of the invention in mammalian cells may involve the construction of cells containing multiple copies of the heterologous BMP-9 gene. The heterologous gene is linked to an amplifiable marker, e.g., the dihydrofolate reductase (DHFR) gene for which cells containing increased gene copies can be selected for propagation in increasing concentrations of methotrexate (MTX) according to the procedures of Kaufman and Sharp, J. Mol. Biol. 159:601–629 (1982). This approach can be employed with a number of different cell types.

For example, a plasmid containing a DNA sequence for a BMP-9 of the invention in operative association with other plasmid sequences enabling expression thereof and the DHFR expression plasmid pAdA26SV(A)3 [Kaufman and Sharp, Mol. Cell. Biol. 2:1304 (1982)] can be co-introduced into DHFR-deficient CHO cells, DUKX-BII, by various methods including calcium phosphate coprecipitation and transfection, electroporation or protoplast fusion. DHFR expressing transformants are selected for growth in alpha media with dialyzed fetal calf serum, and subsequently selected for amplification by growth in increasing concentrations of MTX (e.g., sequential steps in 0.02, 0.2, 1.0 and 5 uM MTX) as described in Kaufman et al., Mol Cell Biol. 5:1750 (1983). Transformants are cloned, and biologically active BMP-9 expression is monitored by the Rosen- modified Sampath-Reddi rat bone formation assay described above in Example III. BMP-9 expression should increase with increasing levels of MTX resistance. BMP-9 polypeptides are characterized using standard techniques known in the art such as pulse labeling with [35S] methionine or cysteine and polyacrylamide gel electrophoresis. Similar procedures can be followed to produce other related BMP-9 proteins.

A. BMP-9 Vector Construction

In order to produce human BMP-9 proteins of the invention DNA sequences encoding the mature region of the human BMP-9 protein may be joined to DNA sequences encoding the propeptide region of the murine BMP-9 protein. This murine/human hybrid DNA sequence is inserted into an appropriate expression vector and introduced into mammalian cells or other preferred eukaryotic or prokaryotic hosts by conventional genetic engineering techniques. The construction of this murine/human BMP-9 containing expression plasmid is described below.

A derivative of the human BMP-9 sequence (SEQ ID NO:8) comprising the nucleotide sequence from nucleotide #105 to #470 (SEQ ID NO:8) is specifically amplified. The following oligonucleotides are utilized as primers to allow the amplification of nucleotides #105 to #470 of the human BMP-9 sequence (SEQ ID NO:8) from clone pGEM-111 described above.

3    ATCGGGCCCCTTTTAGCCAGGCG-GAAAAGGAG (SEQ ID NO:10)

4 AGCGAATTCCCCGCAGGCAGATACTACCTG (SEQ ID NO:11)

This procedure generates the insertion of the nucleotide sequence ATCGGGCCCCT immediately preceding nucleotide #105 (SEQ ID NO:8) and the insertion of the nucleotide sequence GAATTCGCT immediately following nucleotide #470 (SEQ ID NO:8). The addition of these sequences results in the creation of an Apa I and EcoR I restriction endonuclease site at the respective ends of the specifically amplified DNA fragment. The resulting 374 bp Apa I/EcoR I fragment is subcloned into the plasmid vector pGEM-7Zf (+) (Promega catalog# p2251) which has been digested with Apa I and EcoR I. The resulting clone is designated phBMP9mex-1.

The following oligonucleotides are designed on the basis of murine BMP-9 sequences (SEQ ID NO:1) and are modified to facilitate the construction of the murine/human expression plasmid referred to above:

5        GATTCCGTCGACCACCATGTC-CCCTGGGGCCTGGTCTAGATGGATACA-CAGCTGTGGGGCC (SEQ ID NO:12)

6  CCACAGCTGTGTATCCATCTAGACCAG-GCCCCAGGGGACATGGTGGTCGACG (SEQ ID NO:13)

These oligonucleotides contain complimentary sequences which upon addition to each other facilitate the annealing (base pairing) of the two individual sequences, resulting in the formation of a double stranded synthetic DNA linker (designated LINK-1) in a manner indicated below:

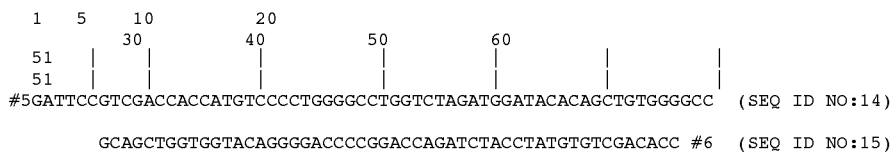

5GATTCCGTCGACCACCATGTCCCCTGGGGCCTGGTCTAGATGGATACACAGCTGTGGGGCC  (SEQ ID NO:14)

GCAGCTGGTGGTACAGGGGACCCCGGACCAGATCTACCTATGTGTCGACACC #6  (SEQ ID NO:15)

This DNA linker (LINK-1) contains recognition sequences of restriction endonucleases needed to facilitate subsequent manipulations required to construct the murine/human expression plasmid, as well as sequences required for maximal expression of heterologous sequences in mammalian cell expression systems. More specifically (referring to the sequence numbering of oligonucleotide #5/LINK-1): nucleotides #1–#11 comprise recognition sequences for the restriction endonucleases BamH I and Sal I, nucleotides #11–#15 allow for maximal expression of heterologous sequences in mammalian cell expression systems, nucleotides #16–#31 correspond to nucleotides #610–#625 of the murine BMP-9 sequence (SEQ ID NO:1), nucleotides #32–#33 are inserted to facilitate efficient restriction digestion of two adjacent restriction endonuclease sites (EcoO109 I and Xba I), nucleotides #34–#60 correspond to nucleotides #1515–#1541 of the murine BMP-9 sequence (SEQ ID NO:1) except that nucleotide #58 of synthetic oligonucleotide #5 is a G rather than the A which appears at position #1539 of SEQ ID NO:1 (This nucleotide conversion results in the creation of an Apa I restriction endonuclease recognition sequence, without altering the amino acid sequence it is intended to encode, to facilitate further manipulations of the murine/human hybrid expression plasmid. LINK-1 (the double stranded product of the annealing of oligonucleotides #5 and #6) is subcloned into the plasmid vector pGEM-7Zf (+) which has been digested with the restriction endonucleases Apa I and BamH I. This results in a plasmid in which the sequences normally present between the Apa I and BamH I sites of the pGEM-7Zf(+) plasmid polylinker are replaced with the sequences of LINK-1 described above. The resulting plasmid clone is designated pBMP-9link. pBMP-9link is digested with the restriction endonucleases BamH I and Xba I resulting in the removal nucleotides #1–#34 of LINK-1 (refer to the numbering of oligo #5).

Clone ML14a, which contains an insert comprising the sequence set forth in SEQ ID NO:1, is also digested with the restriction endonucleases BamH I and Xba I resulting in the removal of sequences comprising nucleotides #1–#1515 of SEQ ID NO:1 (murine BMP-9). This BamH I/Xba I fragment of mouse BMP-9 is isolated from the remainder of the ML14a plasmid clone and subcloned into the BamH I/Xba I sites generated by the removal of the synthetic linker sequences described above. The resulting clone is designated p302.

The p302 clone is digested with the restriction endonuclease EcoO109 I resulting in the excision of nucleotides corresponding to nucleotides #621–#1515 of the murine BMP-9 sequence (SEQ ID NO:1) and nucleotides #35–#59 of LINK-1 (refer to numbering of oligonucleotide #5). It should be noted that the Apa I restriction site created in LINK-1 by the A to G conversion described above is a subset of the recognition sequence of EcoO109 I, therefore digestion of p302 with EcoO109 I cleaves at the Apa I site as well as the naturally occurring murine EcoO109 I (location #619–#625 of SEQ ID NO:1) resulting in the excision of a 920 bp EcoO109 I/EcoO109 I (Apa I) fragment comprising the sequences described above. This 920 EcoO109 I/EcoO109 I (Apa I) fragment is isolated from the remainder of the p302 plasmid clone and subcloned into clone pBMP-9link which has been similarly digested with EcoO109 I. It should be noted that the nucleotides GG (#32–#33 of oligonucleotide #5) originally designed to facilitate a more complete digestion of the two adjacent restriction sites EcoO109 I and Xba I of LINK-1, which is now a part of pBMP-9link (described above), results in the creation of Dcm methylation recognition sequence. The restriction nuclease EcoO109 I is sensitive to Dcm methylation and therefore cleavage of this sequence (nucleotides #25–#31 of oligonucleotide #5/LINK-1) by the restriction endonuclease EcoO109 I is prevented at this site. Therefore the plasmid clone pBMP-9link is cleaved at the Apa I site but not at the EcoO109 I site upon digestion with the restriction endonuclease EcoO109 I as described above, preventing the intended removal of the sequences between the EcoO109 I and Xba I site of LINK-1 (#32–#55 defined by the numbering of oligonucleotide #5). This results in the insertion of the 920 bp EcoO109 I/Apa I fragment at the EcoO109 I (Apa I) site of pBMP-9link. The resulting clone is designated p318.

Clone p318 is digested with the restriction endonucleases Sal I and Apa I, resulting in the excision of sequences comprising nucleotides #6–#56 of LINK-1 (refer to oligo #5 for location), nucleotides #621–#1515 of murine BMP-9 (SEQ ID NO:1), and nucleotides #35–#60 of LINK-1 (refer to oligo #5 for location). The resulting 972 bp Sal I/Apa I fragment described above is isolated from the remainder of the p318 plasmid clone and will be utilized in subsequent manipulations.

The clone phBMP9mex-1 (described above), which contains DNA sequences which encode the entire mature region and portions of the propeptide of the human BMP-9 protein, is digested with the restriction endonucleases Apa I and EcoR I. This results in the excision of a 374 bp fragment comprising nucleotides #105–#470 of the human BMP-9 sequence (SEQ ID NO:8) and the additional nucleotides of oligonucleotide primers #3 and #4 which contain the recognition sequences for the restriction endonucleases Apa I and EcoR I. This 374 bp Apa I/EcoR I fragment is combined with the 972 bp Sal I/Apa I fragment from p138 (isolation described above) and ligated to the mammalian cell expression plasmid pED6 (a derivative of pEMC2β1) which has been digested with Sal I and EcoR I. The resulting clone is designated p324.

The clone ML14a (murine BMP-9) is digested with EcoO109 I and Xba I to generate a fragment comprising nucleotides #621–#1515 of SEQ ID NO:1.

The following oligonucleotides are synthesized on an automated DNA synthesizer and combined such that their complimentary sequences can base pair (anneal) with each other to generate a double stranded synthetic DNA linker designated LINK-2:

7 TCGACCACCATGTCCCCTGG (SEQ ID NO:16)
8 GCCCCAGGGGACATGGTGG (SEQ ID NO:17)

This double stranded synthetic DNA linker (LINK-2) anneals in such a way that it generates single stranded ends which are compatible to DNA fragments digested with Sal I (one end) or EcoO109 I (the other end) as indicated below:

7 TCGACCACCATGTCCCCTGG (SEQ ID NO:18)
GGTGGTACAGGGGACCCCG #8 (SEQ ID NO:19)

This LINK-2 synthetic DNA linker is ligated to the 895 bp EcoO109 I/Xba I fragment comprising nucleotides #621–#1515 of murine BMP-9 (SEQ ID NO:1) described above. This results in a 915 bp Sal I/Xba I fragment.

The clone p324 is digested with Sal I/Xba I to remove sequences comprising nucleotides #6–#56 of LINK-1 (refer to oligo #5 for location) and nucleotides #621–#1515 of murine BMP-9 (SEQ ID NO:1). The sequences comprising nucleotides #35–#60 of LINK-1 (refer to oligo #5 for location) and the sequences comprising the 374 bp Apa I/EcoR I fragment (human BMP-9 sequences) derived from phBMP9mex-1 remain attached to the pED6 backbone. The 915 bp Sal I/Xba I fragment comprising LINK-2 sequences and nucleotides #621–#1515 of murine BMP-9 (SEQ ID NO:1) is ligated into the p324 clone from which the Sal I to Xba I sequences described above have been removed.

The resulting plasmid is designated BMP-9 fusion and comprises LINK-2, nucleotides #621–#1515 of murine BMP-9 (SEQ ID NO:1), nucleotides #35–#59 of LINK-1 (refer to the numbering of oligonucleotide #5), and the 374 bp Apa I/EcoR I fragment (human BMP-9) derived from clone pBMP9mex-1 (described above) inserted between the Sal I and EcoR I sites of the mammalian cell expression vector pED6.

B. Expression

BMP-9 fusion is transfected into CHO cells using standard techniques known to those having ordinary skill in the art to create stable cell lines capable of expressing human BMP-9 protein. The cell lines are cultured under suitable culture conditions and the BMP-9 protein is isolated and purified from the culture medium.

In one embodiment, cells are grown in R1 medium based on a 50:50 mix of F12 and DME plus extra non-essential amino acids plus extra biotin and B12 and 10% fetal bovine serum (FBS) and 0.2 µM methotrexate (MTX). Cells are grown up and expanded into roller bottles in this medium using confluent roller bottles. The serum containing growth medium is discarded, the rollers are rinsed with PBS-CMF, and a serum free production medium is added containing additional amino acids plus insulin (5 µg/ml), putrescine (12.9 µM), hydrocortisone (0.2 µM), selenium (29 µM), and PVA (0.6 g/L). Dextran sulfate is used in this CM (at 100 µg/ml). Conditioned medium (CM) is collected at 24 hours and the rollers are refed with fresh serum free medium. Four sequential 24 hour harvest can be collected. Conditioned medium is clarified (floating cells in the CM are removed) for purification by passing the CM through a 5µ (pass Profile) pore size filter and a 0.22µ (millipore Duropore) pore size filter.

EXAMPLE V
Biological Activity of Expressed BMP-9

To measure the biological activity of the expressed BMP-9 proteins obtained in Example IV above, the proteins are recovered from the cell culture and purified by isolating the BMP-9 proteins from other proteinaceous materials with which they are co-produced as well as from other contaminants. The purified protein may be assayed in accordance with the rat bone formation assay described in Example III.

Purification is carried out using standard techniques known to those skilled in the art. It is contemplated, as with other BMP proteins, that purification may include the use of Heparin sepharose.

In one embodiment, 40 liters of the conditioned media from Example IV-B is titrated to pH 6.9 with concentrated sodium phosphate pH 6.0, and loaded onto Cellufine Sulfate, previously equilibrated with 50 mM sodium phosphate, pH 6.9. The resin is washed with 50 mM sodium phosphate, 0.5 M NaCl, followed by 50 mM sodium phosphate, 0.5 M NaCl, 0.5 M Arg, pH 6.9. BMP-9 is found in the wash as well as the elution, with a lesser amount of contaminants in the elution pool. Cellufine sulfate pools are concentrated and directly loaded onto RP-HPLC for final purification. Each concentrated pool is titrated to pH 3.8 with dilute TFA and loaded onto a 0.46×25 cm $C_4$ reverse phase column running a linear gradient from 30% A (0.1% $TFA/H_2O$) to 55% B (0.1% TFA/90% Acetonitrile) over 100 minutes. BMP-9 monomer is separated by baseline resolution from BMP-9 dimer. The identity of monomer and dimer pools are confirmed by N-terminal sequencing. Although heterogeneity in the N-terminus is expected sequencing reveals a predominant species Ser-Ala-Gly-Ala beginning with amino acid #1 of SEQ ID NO:9.

Protein analysis is conducted using standard techniques such as SDS-PAGE acrylamide [U. K. Laemmli, Nature 227:680 (1970)] stained with silver [R. R. Oakley et al., Anal. Biochem. 105:361 (1980)] and by immunoblot [H. Towbin et al., Proc. Natl. Acad. Sci. USA 76:4350 (1979)]. BMP-9 is efficiently expressed in CHO cells as a 14 kDa nonglycosylated protein when analyzed under reducing conditions. BMP-9 is efficiently secreted within 4 hours of its synthesis.

EXAMPLE VI
A. W-20 Bioassay

Use of the W-20 bone marrow stromal cells as an indicator cell line is based upon the conversion of these cells to osteoblast-like cells after treatment with BMP-2 [R. S. Thies et al., "Bone Morphogenetic Protein alters W-20 stromal cell differentiation in vitro", *Journal of Bone and Mineral Research* 5(2):305 (1990); and R. S. Thies et al., "Recombinant Human Bone Morphogenetic Protein 2 Induces Osteoblastic Differentiation in W-20-17 Stromal Cells", *Endocrinology*, in press (1992)). Specifically, W-20 cells are a clonal bone marrow stromal cell line derived from adult mice by researchers in the laboratory of Dr. D. Nathan, Children's Hospital, Boston, Mass. BMP-2 treatment of W-20 cells results in (1) increased alkaline phosphatase production, (2) induction of PTH stimulated cAMP, and (3) induction of osteocalcin synthesis by the cells. While (1) and (2) represent characteristics associated with the osteoblast phenotype, the ability to synthesize osteocalcin is a phenotypic property only displayed by mature osteoblasts. Furthermore, to date we have observed conversion of W-20 stromal cells to osteoblast-like cells only upon treatment with BMPs. In this manner, the in vitro activities displayed by BMP treated W-20 cells correlate with the in vivo bone forming activity known for BMPS.

Below two in vitro assays useful in comparison of BMP activities of novel osteoinductive molecules are described.

B. W-20 Alkaline Phosphatase Assay Protocol

W-20 cells are plated into 96 well tissue culture plates at a density of 10,000 cells per well in 200 μl of media (DME with 10% heat inactivated fetal calf serum, 2 mM glutamine and 100 U/ml +100 μg/ml streptomycin. The cells are allowed to attach overnight in a 95% air, 5% $CO_2$ incubator at 37° C.

The 200 μl of media is removed from each well with a multichannel pipettor and replaced with an equal volume of test sample delivered in DME with 10% heat inactivated fetal calf serum, 2 mM glutamine and 1% penicillin-streptomycin. Test substances are assayed in triplicate.

The test samples and standards are allowed a 24 hour incubation period with the W-20 indicator cells. After the 24 hours, plates are removed from the 37° C. incubator and the test media are removed from the cells.

The W-20 cell layers are washed 3 times with 200 μl per well of calcium/magnesium free phosphate buffered saline and these washes are discarded.

50 μl of glass distilled water is added to each well and the assay plates are then placed on a dry ice/ethanol bath for quick freezing. Once frozen, the assay plates are removed from the dry ice/ethanol bath and thawed at 37° C. This step is repeated 2 more times for a total of 3 freeze-thaw procedures. Once complete, the membrane bound alkaline phosphatase is available for measurement.

50 μl of assay mix (50 mM glycine, 0.05% Triton X-100, 4 mM $MgCl_2$, 5 mM p-nitrophenol phosphate, pH=10.3) is added to each assay well and the assay plates are then incubated for 30 minutes at 37° C. in a shaking waterbath at 60 oscillations per minute.

At the end of the 30 minute incubation, the reaction is stopped by adding 100 μl of 0.2 N NaOH to each well and placing the assay plates on ice.

The spectrophotometric absorbance for each well is read at a wavelength of 405 nanometers. These values are then compared to known standards to give an estimate of the alkaline phosphatase activity in each sample. For example, using known amounts of p-nitrophenol phosphate, absorbance values are generated. This is shown in Table I.

TABLE I

Absorbance Values for Known Standards of P-Nitrophenol Phosphate

| P-nitrophenol phosphate umoles | Mean absorbance (405 nm) |
| --- | --- |
| 0.000 | 0 |
| 0.006 | 0.261 +/− .024 |
| 0.012 | 0.521 +/− .031 |
| 0.018 | 0.797 +/− .063 |
| 0.024 | 1.074 +/− .061 |
| 0.030 | 1.305 +/− .083 |

Absorbance values for known amounts of BMP-2 can be determined and converted to μmoles of p-nitrophenol phosphate cleaved per unit time as shown in Table II.

TABLE II

Alkaline Phosphatase Values for W-20 Cells Treating with BMP-2

| BMP-2 concentration ng/ml | Absorbance Reading 405 nmeters | umoles substrate per hour |
|---|---|---|
| 0 | 0.645 | 0.024 |
| 1.56 | 0.696 | 0.026 |
| 3.12 | 0.765 | 0.029 |
| 6.25 | 0.923 | 0.036 |
| 12.50 | 1.121 | 0.044 |
| 25.0 | 1.457 | 0.058 |
| 50.0 | 1.662 | 0.067 |
| 100.0 | 1.977 | 0.080 |

These values are then used to compare the activities of known amounts of BMP-9 to BMP-2.

C. Osteocalcin Ria Protocol

W-20 cells are plated at $10^6$ cells per well in 24 well multiwell tissue culture dishes in 2 mls of DME containing 10% heat inactivated fetal calf serum, 2 mM glutamine. The cells are allowed to attach overnight in an atmosphere of 95% air 5% $CO_2$ at 37° C.

The next day the medium is changed to DME containing 10% fetal calf serum, 2 mM glutamine and the test substance in a total volume of 2 ml. Each test substance is administered to triplicate wells. The test substances are incubated with the W-20 cells for a total of 96 hours with replacement at 48 hours by the same test medias.

At the end of 96 hours, 50 µl of the test media is removed from each well and assayed for osteocalcin production using a radioimmunoassay for mouse osteocalcin. The details of the assay are described in the kit manufactured by Biomedical Technologies Inc., 378 Page Street, Stoughton, Mass. 02072. Reagents for the assay are found as product numbers BT-431 (mouse osteocalcin standard), BT-432 (Goat anti-mouse Osteocalcin), BT-431R (iodinated mouse osteocalcin), BT-415 (normal goat serum) and BT-414 (donkey anti goat IgG). The RIA for osteocalcin synthesized by W-20 cells in response to BMP treatment is carried out as described in the protocol provided by the manufacturer.

The values obtained for the test samples are compared to values for known standards of mouse osteocalcin and to the amount of osteocalcin produced by W-20 cells in response to challenge with known amounts of BMP-2.

TABLE III

Osteocalcin Synthesis by W-20 Cells

| BMP-2 Concentration ng/ml | Osteocalcin Synthesis ng/well |
|---|---|
| 0 | 0.8 |
| 2 | 0.9 |
| 4 | 0.8 |
| 8 | 2.2 |
| 16 | 2.7 |
| 31 | 3.2 |
| 62 | 5.1 |
| 125 | 6.5 |
| 250 | 8.2 |
| 500 | 9.4 |
| 1000 | 10.0 |

EXAMPLE VII

Articular Cartilage Assay

The effect of BMP-9 on articular cartilage proteoglycan and DNA synthesis is assayed to determine if BMP-9 is involved in the regulation of metabolism of differentiated articular cartilage.

Articular cartilage explants from calf carpal joints are maintained in DMEM with 50 µg/ml ascorbate, 4 mM glutamine and antibiotics for 3 days. Cytokines (rhBMP-2, rhBMP-4, rhBMP-6 and rhBMP-9, IGF-1, bFGF (1–1000 ng/ml), and TGFβ (1–100 ng/ml)) are added to the medium and culture is continued for 3 more days. Medium is changed daily. Twenty-four hours prior to harvest, explants are pulsed with 50 µCi/ml $^{35}SO_4$ or 25 µCi/ml $^3$H-thymidine. Explants are solubilized and separation of free isotope is performed by gel chromatography. Total DNA of each explant is measured by a spectrophotometric assay. BMP-9 stimulates proteoglycan synthesis above control levels at a dose of 10 ng/ml ($p<0.05$).

BMP-4, BMP-6, BMP-9 and TGFβ are significantly more active in stimulating proteoglycan synthesis at 100 ng/ml. At the highest doses of cytokine tested (1 µg/ml), proteoglycan synthesis by explants exposed to all cytokines are significantly greater ($p<0.05$) than that by control explants. Sulfate incorporation results are set forth in FIG. 4.

Recombinant human BMP-9 stimulates alkaline phosphatase activity in the osteoprogenitor cell line, W-20-17, in a dose responsive manner with an $ED_{50}$ of 4 ng/ml. In vivo, high doses are rhBMP-9 induce ectopic bone formation, with 25 µg/implant of rhBMP-9 inducing cartilage and bone tissue after 10 days of implantation.

It is contemplated that BMP-9 may be used in liver repair or regeneration. Through the use of whole embryo sections or whole mount techniques, expression of mRNA in multiple tissue is screened simultaneously. In the 11.5 dpc mouse embryo, BMP-9 mRNA localizes exclusively to the developing liver. It is contemplated that BMP-9, like all other BMPs studied to date, acts as a local regulator of cell growth and differentiation, therefore this very specific expression pattern suggests liver as a BMP-9 target tissue. BMP-9 responsiveness in parenchymal liver cells is tested by screening four liver cell lines for their ability to bind iodinated, CHO-derived BMP-9. The four liver cell lines, HepG2, NMuli, Chang and NCTC1469, all specifically bound $^{125}$I-BMP-9 to some extent, with HepG2 and NCTC1469 cell lines exhibiting the highest degree of binding. Specific binding of BMP-9 to HepG2 cells is carried out by incubating confluent HepG2 cells with 2 ng/ml $^{125}$I-BMP-9 and increasing concentrations of unlabelled BMP-9 for 20 hours at 4° C. to achieve binding equilibrium. Crosslinking analysis on HepG2 cells with $^{125}$I-BMP-9 yields two binding proteins of apparent molecular weights of 30 and 50 kD. The $K_d$ of the high affinity binding sites for BMP-9 is estimated to be approximately 270 pM for HepG2 cells. Interestingly, the BMP-9 receptors expressed on HepG2 cells show only limited crossreactivity with BMPs 2 and 4, and no crossreactivity with BMPs 3, 5, 6, 7, 12 and 2/6, or with TGF-β1 or TGF-β2. As a first indication of BMP-9 effects on confluent, serum starved HepG2 cells, cell proliferation is examined as determined by $^3$H-thymidine incorporation and cell counting. HepG2 cells are treated for 24 hours with or without BMP-9. $^3$H-thymidine was included during the last 4 hours of treatment. Proliferation was assayed by quantifying ethanol-precipitable $^3$H-thymidine incorporation or counting cells with a hemacytometer BMP-9 stimulates $^3$H-thymidine incorporation in HepG2 cells approximately five fold. This effect is confirmed by a stimulatory effect of BMP-9 in cell counting experiments.

The foregoing descriptions detail presently preferred embodiments of the present invention. Numerous modifications and variations in practice thereof are expected to occur to those skilled in the art upon consideration of these descriptions. Those modifications and variations are believed to be encompassed within the claims appended hereto.

What is claimed is:

1. An isolated DNA molecule which encodes a bone morphogenic protein-9 (BMP-9) comprising a DNA sequence selected from the group consisting of:
   (a) nucleotides 124 through 453 of SEQ ID NO: 8;
   (b) nucleotides 145 through 453 of SEQ ID NO: 8;
   (c) nucleotides 610 through 1893 of SEQ ID NO: 1;
   (d) nucleotides 628 through 1893 of SEQ ID NO: 1;
   (e) nucleotides encoding amino acids 1 or 8 through 110 of SEQ ID NO: 9; and
   (f) nucleotides encoding amino acids 319 or 326 through 428 of SEQ ID NO: 2.

2. A host cell transformed with a DNA molecule of claim 1.

3. A vector comprising a DNA molecule of claim 1 in operative association with an expression control sequence therefor.

4. A host cell transformed with the vector of claim 3.

5. A method for producing a BMP-9, encoded by the DNA molecule according to claim 1 said method comprising the steps of:
   (a) culturing a host cell transformed with said DNA molecule; and
   (b) recovering said BMP-9.

6. A purified BMP-9 encoded by the DNA molecule of claim 1 produced by the steps of:
   (a) culturing a host cell transformed with said DNA molecule; and
   (b) recovering said BMP-9.

7. An isolated DNA sequence encoding BMP-9, said DNA sequence comprising nucleotides 124 through 453 of SEQ ID NO: 8.

8. A method for producing a BMP-9 encoded by the DNA molecule according to claim 7, said method comprising the steps of:
   (a) culturing a host cell transformed with said DNA molecule; and
   (b) recovering said BMP-9.

9. An isolated DNA sequence encoding BMP-9, said DNA sequence comprising nucleotides 145 through 453 of SEQ ID NO: 8.

10. An isolated DNA sequence encoding BMP-9, said DNA sequence comprising nucleotides 610 through 1893 of SEQ ID NO: 1.

11. An isolated DNA sequence encoding BMP-9, said DNA sequence comprising nucleotides 628 through 1893 of SEQ ID NO: 1.

12. A host cell transformed with a DNA of claim 11.

13. An isolated DNA sequence encoding BMP-9, said DNA sequence comprising nucleotides encoding amino acids 1 or 8 through 110 of SEQ ID NO: 9.

14. A host cell transformed with a DNA of claim 13.

15. An isolated DNA sequence encoding BMP-9, said DNA sequence comprising nucleotides encoding amino acids 319 or 326 through 428 of SEQ ID NO: 2.

16. A host cell transformed with a DNA of claim 15.

17. An isolated DNA molecule comprising the DNA sequence of ATCC deposit 75252 encoding BMP-9.

18. A purified BMP-9 comprising an amino acid selected from the group consisting of:
   (a) amino acids 1 or 8 through 110 of SEQ ID NO: 9; and
   (b) amino acids 319 or 326 through 428 of SEQ ID NO: 2.

19. A purified BMP-9 of claim 18, wherein said BMP is a dimer comprising two subunits wherein each of said subunits comprises an amino acid sequence selected from the group consisting of:
   (a) amino acids 1 or 8 through amino acid 110 of SEQ ID NO: 9; and
   (b) amino acids 319 or 326 through amino acid 428 of SEQ ID NO: 2.

20. A pharmaceutical composition comprising the BMP-9 of claim 18 in admixture with a pharmaceutically acceptable vehicle.

21. A composition for bone and/or cartilage formation comprising an amount of a BMP-9 of claim 18 effective for inducing the formation of cartilage and/or bone in a pharmaceutically acceptable vehicle.

22. A composition of claim 21 further comprising a matrix for supporting said composition and providing a surface for bone and/or cartilage growth.

23. A method for inducing formation of cartilage tissue in a patient in need of same comprising administering to said patient a composition comprising an amount of a BMP-9 of claim 18 effective to induce the formation of cartilage tissue.

24. The method of claim 23, wherein said patient has osteoarthritis.

25. A method for inducing bone and/or cartilage formation in a patient in need of same comprising administering to said patient an effective amount of a BMP-9 of claim 18 effective to induce the formation of cartilage and/or bone.

26. A method for inducing growth and differentiation of liver cells, comprising administering a composition comprising an amount effective for inducing the growth and differentiation of liver cells of a bone morphogenetic protein-9 (BMP-9) of claim 18 to said liver cells.

27. A method for stimulating proteoglycan synthesis in differentiated articular cartilage tissue comprising administering a composition comprising an amount effective for stimulating proteoglycan synthesis in differentiated articular cartilage tissue of a bone morphogenetic protein-9 (BMP-9) of claim 18 to said articular cartilage tissue.

28. A purified bone morphogenetic polypeptide (BMP), wherein said BMP is a dimer comprising two subunits wherein one of said subunits comprises an amino acid sequence selected from the group consisting of:
  (a) amino acids 1 or 8 through amino acid 110 of SEQ ID NO:9; and
  (b) amino acids 319 or 326 through amino acid 428 of SEQ ID NO:2; and wherein one of said subunits is selected from the group consisting of a subunit of a BMP selected from the group consisting of BMP-2, BMP-3, BMP-4, BMP-5, BMP-6, BMP-7, and BMP-8.

29. A pharmaceutical composition comprising a BMP of claim 19 or 28 in admixture with a pharmaceutically acceptable vehicle.

* * * * *

SEQUENCE LISTING (1) GENERAL INFORMATION:

(iii) NUMBER OF SEQUENCES: 19

(2) INFORMATION FOR SEQ ID NO:1:

(i) SEQUENCE CHARACTERISTICS:
       (A) LENGTH: 2447 base pairs
       (B) TYPE: nucleic acid
       (C) STRANDEDNESS: double
       (D) TOPOLOGY: linear (ii) MOLECULE TYPE: cDNA to mRNA (iii) HYPOTHETICAL: NO (iv) ANTI-SENSE: NO (vi) ORIGINAL SOURCE:
       (A) ORGANISM: Mus musculus
       (B) STRAIN: C57B46xCBA
       (F) TISSUE TYPE: liver (vii) IMMEDIATE SOURCE:
       (A) LIBRARY: Mouse liver cDNA
       (B) CLONE: ML14A (viii) POSITION IN GENOME:
       (C) UNITS: bp (ix) FEATURE:
       (A) NAME/KEY: mat_peptide
       (B) LOCATION: 1564..1893

(ix) FEATURE:
       (A) NAME/KEY: CDS
       (B) LOCATION: 610..1896

(ix) FEATURE:
       (A) NAME/KEY: mRNA
       (B) LOCATION: 1..2447

(xi) SEQUENCE DESCRIPTION: SEQ ID NO:1:

```
CATTAATAAA TATTAAGTAT TGGAATTAGT GAAATTGGAG TTCCTTGTGG AAGGAAGTGG      60

GCAAGTGAGC TTTTTAGTTT GTGTCGGAAG CCTGTAATTA CGGCTCCAGC TCATAGTGGA     120

ATGGCTATAC TTAGATTTAT GGATAGTTGG GTAGTAGGTG TAAATGTATG TGGTAAAAGG     180

CCTAGGAGAT TTGTTGATCC AATAAATATG ATTAGGGAAA CAATTATTAG GGTTCATGTT     240

CGTCCTTTTG GTGTGTGGAT TAGCATTATT TGTTTGATAA TAAGTTTAAC TAGTCAGTGT     300

TGGAAAGAAT GGAGACGGTT GTTGATTAGG CGTTTTGAGG ATGGGAATAG GATTGAAGGA     360

AATATAATGA TGGCTACAAC GATTGGGAAT CCTATTATTG TTGGGGTAAT GAATGAGGCA     420

AATAGATTTT CGTTCATTTT AATTCTCAAG GGGTTTTTAC TTTTATGTTT GTTAGTGATA     480

TTGGTGAGTA GGCCAAGGGT TAATAGTGTA ATTGAATTAT AGTGAAATCA TATTACTAGA     540

CCTGATGTTA GAAGGAGGGC TGAAAAGGCT CCTTCCCTCC CAGGACAAAA CCGGAGCAGG     600

GCCACCCGG ATG TCC CCT GGG GCC TTC CGG GTG GCC CTG CTC CCG CTG         648
           Met Ser Pro Gly Ala Phe Arg Val Ala Leu Leu Pro Leu
           -318         -315                 -310

TTC CTG CTG GTC TGT GTC ACA CAG CAG AAG CCG CTG CAG AAC TGG GAA        696
Phe Leu Leu Val Cys Val Thr Gln Gln Lys Pro Leu Gln Asn Trp Glu
-305                 -300                 -295                 -290

CAA GCA TCC CCT GGG GAA AAT GCC CAC AGC TCC CTG GGA TTG TCT GGA        744
Gln Ala Ser Pro Gly Glu Asn Ala His Ser Ser Leu Gly Leu Ser Gly
            -285                 -280                 -275
```

```
GCT GGA GAG GAG GGT GTC TTT GAC CTG CAG ATG TTC CTG GAG AAC ATG        792
Ala Gly Glu Glu Gly Val Phe Asp Leu Gln Met Phe Leu Glu Asn Met
            -270                -265                -260

AAG GTG GAT TTC CTA CGC AGC CTT AAC CTC AGC GGC ATT CCC TCC CAG        840
Lys Val Asp Phe Leu Arg Ser Leu Asn Leu Ser Gly Ile Pro Ser Gln
        -255                -250                -245

GAC AAA ACC AGA GCG GAG CCA CCC CAG TAC ATG ATC GAC TTG TAC AAC        888
Asp Lys Thr Arg Ala Glu Pro Pro Gln Tyr Met Ile Asp Leu Tyr Asn
        -240                -235            -230

AGA TAC ACA ACG GAC AAA TCG TCT ACG CCT GCC TCC AAC ATC GTG CGG        936
Arg Tyr Thr Thr Asp Lys Ser Ser Thr Pro Ala Ser Asn Ile Val Arg
-225                -220                -215                -210

AGC TTC AGC GTG GAA GAT GCT ATA TCG ACA GCT GCC ACG GAG GAC TTC        984
Ser Phe Ser Val Glu Asp Ala Ile Ser Thr Ala Ala Thr Glu Asp Phe
            -205                -200                -195

CCC TTT CAG AAG CAC ATC CTG ATC TTC AAC ATC TCC ATC CCG AGG CAC       1032
Pro Phe Gln Lys His Ile Leu Ile Phe Asn Ile Ser Ile Pro Arg His
            -190                -185            -180

GAG CAG ATC ACC AGG GCT GAG CTC CGA CTC TAT GTC TCC TGC CAA AAT       1080
Glu Gln Ile Thr Arg Ala Glu Leu Arg Leu Tyr Val Ser Cys Gln Asn
        -175                -170                -165

GAT GTG GAC TCC ACT CAT GGG CTG GAA GGA AGC ATG GTC GTT TAT GAT       1128
Asp Val Asp Ser Thr His Gly Leu Glu Gly Ser Met Val Val Tyr Asp
    -160                -155                -150

GTT CTG GAG GAC AGT GAG ACT TGG GAC CAG GCC ACG GGG ACC AAG ACC       1176
Val Leu Glu Asp Ser Glu Thr Trp Asp Gln Ala Thr Gly Thr Lys Thr
-145                -140                -135                -130

TTC TTG GTA TCC CAG GAC ATT CGG GAC GAA GGA TGG GAG ACT TTA GAA       1224
Phe Leu Val Ser Gln Asp Ile Arg Asp Glu Gly Trp Glu Thr Leu Glu
            -125                -120                -115

GTA TCG AGT GCC GTG AAG CGG TGG GTC AGG GCA GAC TCC ACA ACA AAC       1272
Val Ser Ser Ala Val Lys Arg Trp Val Arg Ala Asp Ser Thr Thr Asn
            -110                -105                -100

AAA AAT AAG CTC GAG GTG ACA GTG CAG AGC CAC AGG GAG AGC TGT GAC       1320
Lys Asn Lys Leu Glu Val Thr Val Gln Ser His Arg Glu Ser Cys Asp
        -95                 -90                 -85

ACA CTG GAC ATC AGT GTC CCT CCA GGT TCC AAA AAC CTG CCC TTC TTT       1368
Thr Leu Asp Ile Ser Val Pro Pro Gly Ser Lys Asn Leu Pro Phe Phe
    -80                 -75                 -70

GTT GTC TTC TCC AAT GAC CGC AGC AAT GGG ACC AAG GAG ACC AGA CTG       1416
Val Val Phe Ser Asn Asp Arg Ser Asn Gly Thr Lys Glu Thr Arg Leu
-65                 -60                 -55                 -50

GAG CTG AAG GAG ATG ATC GGC CAT GAG CAG GAG ACC ATG CTT GTG AAG       1464
Glu Leu Lys Glu Met Ile Gly His Glu Gln Glu Thr Met Leu Val Lys
            -45                 -40                 -35

ACA GCC AAA AAT GCT TAC CAG GTG GCA GGT GAG AGC CAA GAG GAG GAG       1512
Thr Ala Lys Asn Ala Tyr Gln Val Ala Gly Glu Ser Gln Glu Glu Glu
        -30                 -25                 -20

GGT CTA GAT GGA TAC ACA GCT GTG GGA CCA CTT TTA GCT AGA AGG AAG       1560
Gly Leu Asp Gly Tyr Thr Ala Val Gly Pro Leu Leu Ala Arg Arg Lys
        -15                 -10                 -5

AGG AGC ACC GGA GCC AGC AGC CAC TGC CAG AAG ACT TCT CTC AGG GTG       1608
Arg Ser Thr Gly Ala Ser Ser His Cys Gln Lys Thr Ser Leu Arg Val
    1                   5                   10                  15

AAC TTT GAG GAC ATC GGC TGG GAC AGC TGG ATC ATT GCA CCC AAG GAA       1656
Asn Phe Glu Asp Ile Gly Trp Asp Ser Trp Ile Ile Ala Pro Lys Glu
                    20                  25                  30

TAT GAC GCC TAT GAG TGT AAA GGG GGT TGC TTC TTC CCA TTG GCT GAT       1704
Tyr Asp Ala Tyr Glu Cys Lys Gly Gly Cys Phe Phe Pro Leu Ala Asp
```

```
                    35                    40                       45
GAC GTG ACA CCC ACC AAA CAT GCC ATC GTG CAG ACC CTG GTG CAT CTC     1752
Asp Val Thr Pro Thr Lys His Ala Ile Val Gln Thr Leu Val His Leu
            50                   55                   60

GAG TTC CCC ACA AAG GTG GGC AAA GCC TGC TGC GTT CCC ACC AAA CTG     1800
Glu Phe Pro Thr Lys Val Gly Lys Ala Cys Cys Val Pro Thr Lys Leu
        65                  70                  75

AGT CCC ATC TCC ATC CTC TAC AAG GAT GAC ATG GGG GTG CCA ACC CTC     1848
Ser Pro Ile Ser Ile Leu Tyr Lys Asp Asp Met Gly Val Pro Thr Leu
80                  85                  90                  95

AAG TAC CAC TAT GAG GGG ATG AGT GTG GCT GAG TGT GGG TGT AGG TAGTCCCT 1903
Lys Tyr His Tyr Glu Gly Met Ser Val Ala Glu Cys Gly Cys Arg
                100                 105                 110

AGCCACCCAG GGTGGGGATA CAGGACATGG AAGAGGTTCT GGTACGGTCC TGCATCCTCC    1963

TGCGCATGGT ATGCCTAAGT TGATCAGAAA CCATCCTTGA GAAGAAAGG AGTTAGTTGC     2023

CCTTCTTGTG TCTGGTGGGT CCCTCTGCTG AAGTGACAAT GACTGGGGTA TGCGGGCCTG    2083

TGGGCAGAGC AGGAGACCCT GGAAGGGTTA GTGGGTAGAA AGATGTCAAA AAGGAAGCTG    2143

TGGGTAGATG ACCTGCACTC CAGTGATTAG AAGTCCAGCC TTACCTGTGA GAGAGCTCCT    2203

GGCATCTAAG AGAACTCTGC TTCCTCATCA TCCCCACCGA CTTGTTCTTC CTTGGGAGTG    2263

TGTCCTCAGG GAGAACAGCA TTGCTGTTCC TGTGCCTCAA GCTCCCAGCT GACTCTCCTG    2323

TGGCTCATAG GACTGAATGG GGTGAGGAAG AGCCTGATGC CCTCTGGCAA TCAGAGCCCG    2383

AAGGACTTCA AAACATCTGG ACAACTCTCA TTGACTGATG CTCCAACATA ATTTTTAAAA    2443

AGAG                                                                 2447

(2) INFORMATION FOR SEQ ID NO:2:

(i) SEQUENCE CHARACTERISTICS:
        (A) LENGTH: 428 amino acids
        (B) TYPE: amino acid
        (D) TOPOLOGY: linear (ii) MOLECULE TYPE: protein (xi) SEQUENCE DESCRIPTION: SEQ ID NO:2:

Met Ser Pro Gly Ala Phe Arg Val Ala Leu Leu Pro Leu Phe Leu Leu
-318         -315              -310             -305

Val Cys Val Thr Gln Gln Lys Pro Leu Gln Asn Trp Glu Gln Ala Ser
        -300             -295             -290

Pro Gly Glu Asn Ala His Ser Ser Leu Gly Leu Ser Gly Ala Gly Glu
    -285             -280             -275

Glu Gly Val Phe Asp Leu Gln Met Phe Leu Glu Asn Met Lys Val Asp
-270             -265             -260             -255

Phe Leu Arg Ser Leu Asn Leu Ser Gly Ile Pro Ser Gln Asp Lys Thr
             -250             -245             -240

Arg Ala Glu Pro Pro Gln Tyr Met Ile Asp Leu Tyr Asn Arg Tyr Thr
             -235             -230             -225

Thr Asp Lys Ser Ser Thr Pro Ala Ser Asn Ile Val Arg Ser Phe Ser
            -220             -215             -210

Val Glu Asp Ala Ile Ser Thr Ala Ala Thr Glu Asp Phe Pro Phe Gln
    -205             -200             -195

Lys His Ile Leu Ile Phe Asn Ile Ser Ile Pro Arg His Glu Gln Ile
-190             -185             -180             -175

Thr Arg Ala Glu Leu Arg Leu Tyr Val Ser Cys Gln Asn Asp Val Asp
            -170             -165             -160
```

```
Ser Thr His Gly Leu Glu Gly Ser Met Val Val Tyr Asp Val Leu Glu
        -155             -150            -145

Asp Ser Glu Thr Trp Asp Gln Ala Thr Gly Thr Lys Thr Phe Leu Val
        -140             -135            -130

Ser Gln Asp Ile Arg Asp Glu Gly Trp Glu Thr Leu Glu Val Ser Ser
        -125             -120            -115

Ala Val Lys Arg Trp Val Arg Ala Asp Ser Thr Thr Asn Lys Asn Lys
-110            -105             -100            -95

Leu Glu Val Thr Val Gln Ser His Arg Glu Ser Cys Asp Thr Leu Asp
        -90              -85             -80

Ile Ser Val Pro Pro Gly Ser Lys Asn Leu Pro Phe Phe Val Val Phe
        -75              -70             -65

Ser Asn Asp Arg Ser Asn Gly Thr Lys Glu Thr Arg Leu Glu Leu Lys
        -60              -55             -50

Glu Met Ile Gly His Glu Gln Glu Thr Met Leu Val Lys Thr Ala Lys
        -45              -40             -35

Asn Ala Tyr Gln Val Ala Gly Glu Ser Gln Glu Glu Gly Leu Asp
-30             -25              -20             -15

Gly Tyr Thr Ala Val Gly Pro Leu Leu Ala Arg Arg Lys Arg Ser Thr
        -10              -5                      1

Gly Ala Ser Ser His Cys Gln Lys Thr Ser Leu Arg Val Asn Phe Glu
        5                10                      15

Asp Ile Gly Trp Asp Ser Trp Ile Ile Ala Pro Lys Glu Tyr Asp Ala
        20               25                      30

Tyr Glu Cys Lys Gly Gly Cys Phe Phe Pro Leu Ala Asp Asp Val Thr
35              40                       45                     50

Pro Thr Lys His Ala Ile Val Gln Thr Leu Val His Leu Glu Phe Pro
                55                       60                      65

Thr Lys Val Gly Lys Ala Cys Cys Val Pro Thr Lys Leu Ser Pro Ile
                70                       75                      80

Ser Ile Leu Tyr Lys Asp Asp Met Gly Val Pro Thr Leu Lys Tyr His
                85                       90                      95

Tyr Glu Gly Met Ser Val Ala Glu Cys Gly Cys Arg
100             105                      110

(2) INFORMATION FOR SEQ ID NO:3:

(i) SEQUENCE CHARACTERISTICS:
        (A) LENGTH: 1954 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (A) ORGANISM: Homo sapiens
        (G) CELL TYPE: Osteosarcoma Cell Line
        (H) CELL LINE: U-2OS (vii) IMMEDIATE SOURCE:
        (A) LIBRARY: U2OS cDNA in Lambda gt10
        (B) CLONE: Lambda U2OS-3

(viii) POSITION IN GENOME:
        (C) UNITS: bp
```

(ix) FEATURE:
            (A) NAME/KEY: CDS
            (B) LOCATION: 403..1629

(ix) FEATURE:
            (A) NAME/KEY: mat_peptide
            (B) LOCATION: 1279..1626

(ix) FEATURE:
            (A) NAME/KEY: mRNA
            (B) LOCATION: 9..1934

(xi) SEQUENCE DESCRIPTION: SEQ ID NO:3:

```
CTCTAGAGGG CAGAGGAGGA GGGAGGGAGG GAAGGAGCGC GGAGCCCGGC CCGGAAGCTA       60

GGTGAGTGTG GCATCCGAGC TGAGGGACGC GAGCCTGAGA CGCCGCTGCT GCTCCGGCTG      120

AGTATCTAGC TTGTCTCCCC GATGGGATTC CCGTCCAAGC TATCTCGAGC CTGCAGCGCC      180

ACAGTCCCCG GCCCTCGCCC AGGTTCACTG CAACCGTTCA GAGGTCCCCA GGAGCTGCTG      240

CTGGCGAGCC CGCTACTGCA GGGACCTATG GAGCCATTCC GTAGTGCCAT CCCGAGCAAC      300

GCACTGCTGC AGCTTCCCTG AGCCTTTCCA GCAAGTTTGT TCAAGATTGG CTGTCAAGAA      360

TCATGGACTG TTATTATATG CCTTGTTTTC TGTCAAGACA CC ATG ATT CCT GGT         414
                                                Met Ile Pro Gly
                                                -292    -290
```

| AAC CGA ATG CTG ATG GTC GTT TTA TTA TGC CAA GTC CTG CTA GGA GGC | 462 |
|---|---|
| Asn Arg Met Leu Met Val Val Leu Leu Cys Gln Val Leu Leu Gly Gly | |
|     -285            -280            -275 | |

```
GCG AGC CAT GCT AGT TTG ATA CCT GAG ACG GGG AAG AAA AAA GTC GCC       510
Ala Ser His Ala Ser Leu Ile Pro Glu Thr Gly Lys Lys Lys Val Ala
        -270            -265            -260

GAG ATT CAG GGC CAC GCG GGA GGA CGC CGC TCA GGG CAG AGC CAT GAG       558
Glu Ile Gln Gly His Ala Gly Gly Arg Arg Ser Gly Gln Ser His Glu
    -255            -250            -245

CTC CTG CGG GAC TTC GAG GCG ACA CTT CTG CAG ATG TTT GGG CTG CGC       606
Leu Leu Arg Asp Phe Glu Ala Thr Leu Leu Gln Met Phe Gly Leu Arg
-240            -235            -230                -225

CGC CGC CCG CAG CCT AGC AAG AGT GCC GTC ATT CCG GAC TAC ATG CGG       654
Arg Arg Pro Gln Pro Ser Lys Ser Ala Val Ile Pro Asp Tyr Met Arg
            -220            -215            -210

GAT CTT TAC CGG CTT CAG TCT GGG GAG GAG GAG GAA GAG CAG ATC CAC       702
Asp Leu Tyr Arg Leu Gln Ser Gly Glu Glu Glu Glu Glu Gln Ile His
        -205            -200            -195

AGC ACT GGT CTT GAG TAT CCT GAG CGC CCG GCC AGC CGG GCC AAC ACC       750
Ser Thr Gly Leu Glu Tyr Pro Glu Arg Pro Ala Ser Arg Ala Asn Thr
        -190            -185            -180

GTG AGG AGC TTC CAC CAC GAA GAA CAT CTG GAG AAC ATC CCA GGG ACC       798
Val Arg Ser Phe His His Glu Glu His Leu Glu Asn Ile Pro Gly Thr
    -175            -170            -165

AGT GAA AAC TCT GCT TTT CGT TTC CTC TTT AAC CTC AGC AGC ATC CCT       846
Ser Glu Asn Ser Ala Phe Arg Phe Leu Phe Asn Leu Ser Ser Ile Pro
-160            -155            -150                -145

GAG AAC GAG GTG ATC TCC TCT GCA GAG CTT CGG CTC TTC CGG GAG CAG       894
Glu Asn Glu Val Ile Ser Ser Ala Glu Leu Arg Leu Phe Arg Glu Gln
            -140            -135            -130

GTG GAC CAG GGC CCT GAT TGG GAA AGG GGC TTC CAC CGT ATA AAC ATT       942
Val Asp Gln Gly Pro Asp Trp Glu Arg Gly Phe His Arg Ile Asn Ile
        -125            -120            -115

TAT GAG GTT ATG AAG CCC CCA GCA GAA GTG GTG CCT GGG CAC CTC ATC       990
Tyr Glu Val Met Lys Pro Pro Ala Glu Val Val Pro Gly His Leu Ile
        -110            -105            -100

ACA CGA CTA CTG GAC ACG AGA CTG GTC CAC CAC AAT GTG ACA CGG TGG      1038
```

-continued

```
Thr Arg Leu Leu Asp Thr Arg Leu Val His His Asn Val Thr Arg Trp
    -95             -90                 -85

GAA ACT TTT GAT GTG AGC CCT GCG GTC CTT CGC TGG ACC CGG GAG AAG      1086
Glu Thr Phe Asp Val Ser Pro Ala Val Leu Arg Trp Thr Arg Glu Lys
-80                 -75                 -70                 -65

CAG CCA AAC TAT GGG CTA GCC ATT GAG GTG ACT CAC CTC CAT CAG ACT      1134
Gln Pro Asn Tyr Gly Leu Ala Ile Glu Val Thr His Leu His Gln Thr
                -60                 -55                 -50

CGG ACC CAC CAG GGC CAG CAT GTC AGG ATT AGC CGA TCG TTA CCT CAA      1182
Arg Thr His Gln Gly Gln His Val Arg Ile Ser Arg Ser Leu Pro Gln
            -45                 -40                 -35

GGG AGT GGG AAT TGG GCC CAG CTC CGG CCC CTC CTG GTC ACC TTT GGC      1230
Gly Ser Gly Asn Trp Ala Gln Leu Arg Pro Leu Leu Val Thr Phe Gly
        -30                 -25                 -20

CAT GAT GGC CGG GGC CAT GCC TTG ACC CGA CGC CGG AGG GCC AAG CGT      1278
His Asp Gly Arg Gly His Ala Leu Thr Arg Arg Arg Ala Lys Arg
    -15                 -10                 -5

AGC CCT AAG CAT CAC TCA CAG CGG GCC AGG AAG AAG AAT AAG AAC TGC      1326
Ser Pro Lys His His Ser Gln Arg Ala Arg Lys Lys Asn Lys Asn Cys
 1           5                  10                  15

CGG CGC CAC TCG CTC TAT GTG GAC TTC AGC GAT GTG GGC TGG AAT GAC      1374
Arg Arg His Ser Leu Tyr Val Asp Phe Ser Asp Val Gly Trp Asn Asp
             20                  25                  30

TGG ATT GTG GCC CCA CCA GGC TAC CAG GCC TTC TAC TGC CAT GGG GAC      1422
Trp Ile Val Ala Pro Pro Gly Tyr Gln Ala Phe Tyr Cys His Gly Asp
         35                  40                  45

TGC CCC TTT CCA CTG GCT GAC CAC CTC AAC TCA ACC AAC CAT GCC ATT      1470
Cys Pro Phe Pro Leu Ala Asp His Leu Asn Ser Thr Asn His Ala Ile
     50                  55                  60

GTG CAG ACC CTG GTC AAT TCT GTC AAT TCC AGT ATC CCC AAA GCC TGT      1518
Val Gln Thr Leu Val Asn Ser Val Asn Ser Ser Ile Pro Lys Ala Cys
 65                  70                  75                  80

TGT GTG CCC ACT GAA CTG AGT GCC ATC TCC ATG CTG TAC CTG GAT GAG      1566
Cys Val Pro Thr Glu Leu Ser Ala Ile Ser Met Leu Tyr Leu Asp Glu
             85                  90                  95

TAT GAT AAG GTG GTA CTG AAA AAT TAT CAG GAG ATG GTA GTA GAG GGA      1614
Tyr Asp Lys Val Val Leu Lys Asn Tyr Gln Glu Met Val Val Glu Gly
         100                 105                 110

TGT GGG TGC CGC TGAGATCAGG CAGTCCTTGA GGATAGACAG ATATACACAC          1666
Cys Gly Cys Arg
         115

CACACACACA CACCACATAC ACCACACACA CACGTTCCCA TCCACTCACC CACACACTAC    1726

ACAGACTGCT TCCTTATAGC TGGACTTTTA TTTAAAAAAA AAAAAAAAAA AATGGAAAAA    1786

ATCCCTAAAC ATTCACCTTG ACCTTATTTA TGACTTTACG TGCAAATGTT TTGACCATAT    1846

TGATCATATA TTTTGACAAA ATATATTTAT AACTACGTAT TAAAAGAAAA AAATAAAATG    1906

AGTCATTATT TTAAAAAAAA AAAAAAAACT CTAGAGTCGA CGGAATTC                 1954
```

(2) INFORMATION FOR SEQ ID NO:4:

(i) SEQUENCE CHARACTERISTICS:
        (A) LENGTH: 408 amino acids
        (B) TYPE: amino acid
        (D) TOPOLOGY: linear (ii) MOLECULE TYPE: protein (xi) SEQUENCE DESCRIPTION: SEQ ID NO:4:

```
Met Ile Pro Gly Asn Arg Met Leu Met Val Val Leu Leu Cys Gln Val
-292      -290                -285                -280
```

-continued

```
Leu Leu Gly Gly Ala Ser His Ala Ser Leu Ile Pro Glu Thr Gly Lys
    -275              -270              -265
Lys Lys Val Ala Glu Ile Gln Gly His Ala Gly Gly Arg Arg Ser Gly
-260              -255              -250              -245
Gln Ser His Glu Leu Leu Arg Asp Phe Glu Ala Thr Leu Leu Gln Met
             -240              -235              -230
Phe Gly Leu Arg Arg Arg Pro Gln Pro Ser Lys Ser Ala Val Ile Pro
             -225              -220              -215
Asp Tyr Met Arg Asp Leu Tyr Arg Leu Gln Ser Gly Glu Glu Glu
             -210              -205              -200
Glu Gln Ile His Ser Thr Gly Leu Glu Tyr Pro Glu Arg Pro Ala Ser
    -195              -190              -185
Arg Ala Asn Thr Val Arg Ser Phe His His Glu Glu His Leu Glu Asn
-180              -175              -170              -165
Ile Pro Gly Thr Ser Glu Asn Ser Ala Phe Arg Phe Leu Phe Asn Leu
             -160              -155              -150
Ser Ser Ile Pro Glu Asn Glu Val Ile Ser Ser Ala Glu Leu Arg Leu
             -145              -140              -135
Phe Arg Glu Gln Val Asp Gln Gly Pro Asp Trp Glu Arg Gly Phe His
             -130              -125              -120
Arg Ile Asn Ile Tyr Glu Val Met Lys Pro Pro Ala Glu Val Val Pro
    -115              -110              -105
Gly His Leu Ile Thr Arg Leu Leu Asp Thr Arg Leu Val His His Asn
-100               -95               -90               -85
Val Thr Arg Trp Glu Thr Phe Asp Val Ser Pro Ala Val Leu Arg Trp
              -80               -75               -70
Thr Arg Glu Lys Gln Pro Asn Tyr Gly Leu Ala Ile Glu Val Thr His
              -65               -60               -55
Leu His Gln Thr Arg Thr His Gln Gly Gln His Val Arg Ile Ser Arg
              -50               -45               -40
Ser Leu Pro Gln Gly Ser Gly Asn Trp Ala Gln Leu Arg Pro Leu Leu
    -35               -30               -25
Val Thr Phe Gly His Asp Gly Arg Gly His Ala Leu Thr Arg Arg Arg
-20               -15               -10                                -5
Arg Ala Lys Arg Ser Pro Lys His His Ser Gln Arg Ala Arg Lys Lys
              1                 5                 10
Asn Lys Asn Cys Arg Arg His Ser Leu Tyr Val Asp Phe Ser Asp Val
    15                20                25
Gly Trp Asn Asp Trp Ile Val Ala Pro Pro Gly Tyr Gln Ala Phe Tyr
    30                35                40
Cys His Gly Asp Cys Pro Phe Pro Leu Ala Asp His Leu Asn Ser Thr
45                50                55                60
Asn His Ala Ile Val Gln Thr Leu Val Asn Ser Val Asn Ser Ser Ile
              65                70                75
Pro Lys Ala Cys Cys Val Pro Thr Glu Leu Ser Ala Ile Ser Met Leu
              80                85                90
Tyr Leu Asp Glu Tyr Asp Lys Val Val Leu Lys Asn Tyr Gln Glu Met
         95               100               105
Val Val Glu Gly Cys Gly Cys Arg
    110               115
```

(2) INFORMATION FOR SEQ ID NO:5:

(i) SEQUENCE CHARACTERISTICS:
        (A) LENGTH: 15 base pairs
        (B) TYPE: nucleic acid
        (C) STRANDEDNESS: double
        (D) TOPOLOGY: linear (ii) MOLECULE TYPE: cDNA to mRNA (xi) SEQUENCE DESCRIPTION: SEQ ID NO:5:

CATGGGCAGC TCGAG                                                          15

(2) INFORMATION FOR SEQ ID NO:6:

(i) SEQUENCE CHARACTERISTICS:
        (A) LENGTH: 34 base pairs
        (B) TYPE: nucleic acid
        (C) STRANDEDNESS: double
        (D) TOPOLOGY: linear (ii) MOLECULE TYPE: cDNA to mRNA (xi) SEQUENCE DESCRIPTION: SEQ ID NO:6:

CTGCAGGCGA GCCTGAATTC CTCGAGCCAT CATG                                     34

(2) INFORMATION FOR SEQ ID NO:7:

(i) SEQUENCE CHARACTERISTICS:
        (A) LENGTH: 68 base pairs
        (B) TYPE: nucleic acid
        (C) STRANDEDNESS: double
        (D) TOPOLOGY: linear (ii) MOLECULE TYPE: cDNA to mRNA (xi) SEQUENCE DESCRIPTION: SEQ ID NO:7:

CGAGGTTAAA AAACGTCTAG GCCCCCCGAA CCACGGGGAC GTGGTTTTCC TTTGAAAAAC         60
ACGATTGC                                                                 68

(2) INFORMATION FOR SEQ ID NO:8:

(i) SEQUENCE CHARACTERISTICS:
        (A) LENGTH: 470 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (v) FRAGMENT TYPE: C-terminal (vi) ORIGINAL SOURCE:
        (A) ORGANISM: Homo sapiens
        (H) CELL LINE: W138 (genomic DNA)

(vii) IMMEDIATE SOURCE:
        (A) LIBRARY: human genomic library
        (B) CLONE: lambda 111-1

(viii) POSITION IN GENOME:
        (C) UNITS: bp (ix) FEATURE:
        (A) NAME/KEY: exon
        (B) LOCATION: 1..470

(ix) FEATURE:
        (A) NAME/KEY: CDS
        (B) LOCATION: 1..456

(ix) FEATURE:

(A) NAME/KEY: mat_peptide
            (B) LOCATION: 124..453

(ix) FEATURE:
            (A) NAME/KEY: mRNA
            (B) LOCATION: 1..470

(xi) SEQUENCE DESCRIPTION: SEQ ID NO:8:

```
TGA ACA AGA GAG TGC TCA AGA AGC TGT CCA AGG ACG GCT CCA CAG AGG     48
    Thr Arg Glu Cys Ser Arg Ser Cys Pro Arg Thr Ala Pro Gln Arg
-41 -40             -35             -30

CAG GTG AGA GCA GTC ACG AGG AGG ACA CGG ATG GCG CAC GTG GCT GCG     96
Gln Val Arg Ala Val Thr Arg Arg Thr Arg Met Ala His Val Ala Ala
-25             -20             -15             -10

GGG TCG ACT TTA GCC AGG CGG AAA AGG AGC GCC GGG GCT GGC AGC CAC    144
Gly Ser Thr Leu Ala Arg Arg Lys Arg Ser Ala Gly Ala Gly Ser His
                -5              1               5

TGT CAA AAG ACC TCC CTG CGG GTA AAC TTC GAG GAC ATC GGC TGG GAC    192
Cys Gln Lys Thr Ser Leu Arg Val Asn Phe Glu Asp Ile Gly Trp Asp
        10              15              20

AGC TGG ATC ATT GCA CCC AAG GAG TAT GAA GCC TAC GAG TGT AAG GGC    240
Ser Trp Ile Ile Ala Pro Lys Glu Tyr Glu Ala Tyr Glu Cys Lys Gly
    25              30              35

GGC TGC TTC TTC CCC TTG GCT GAC GAT GTG ACG CCG ACG AAA CAC GCT    288
Gly Cys Phe Phe Pro Leu Ala Asp Asp Val Thr Pro Thr Lys His Ala
40              45              50              55

ATC GTG CAG ACC CTG GTG CAT CTC AAG TTC CCC ACA AAG GTG GGC AAG    336
Ile Val Gln Thr Leu Val His Leu Lys Phe Pro Thr Lys Val Gly Lys
            60              65              70

GCC TGC TGT GTG CCC ACC AAA CTG AGC CCC ATC TCC GTC CTC TAC AAG    384
Ala Cys Cys Val Pro Thr Lys Leu Ser Pro Ile Ser Val Leu Tyr Lys
        75              80              85

GAT GAC ATG GGG GTG CCC ACC CTC AAG TAC CAT TAC GAG GGC ATG AGC    432
Asp Asp Met Gly Val Pro Thr Leu Lys Tyr His Tyr Glu Gly Met Ser
    90              95              100

GTG GCA GAG TGT GGG TGC AGG TAGTATCTGC CTGCGGG                      470
Val Ala Glu Cys Gly Cys Arg
    105             110
```

(2) INFORMATION FOR SEQ ID NO:9:

(i) SEQUENCE CHARACTERISTICS:
            (A) LENGTH: 150 amino acids
            (B) TYPE: amino acid
            (D) TOPOLOGY: linear (ii) MOLECULE TYPE: protein (xi) SEQUENCE DESCRIPTION: SEQ ID NO:9:

```
    Thr Arg Glu Cys Ser Arg Ser Cys Pro Arg Thr Ala Pro Gln Arg
-41 -40             -35             -30

Gln Val Arg Ala Val Thr Arg Arg Thr Arg Met Ala His Val Ala Ala
-25             -20             -15             -10

Gly Ser Thr Leu Ala Arg Arg Lys Arg Ser Ala Gly Ala Gly Ser His
                -5              1               5

Cys Gln Lys Thr Ser Leu Arg Val Asn Phe Glu Asp Ile Gly Trp Asp
        10              15              20

Ser Trp Ile Ile Ala Pro Lys Glu Tyr Glu Ala Tyr Glu Cys Lys Gly
    25              30              35

Gly Cys Phe Phe Pro Leu Ala Asp Asp Val Thr Pro Thr Lys His Ala
40              45              50              55
```

```
Ile Val Gln Thr Leu Val His Leu Lys Phe Pro Thr Lys Val Gly Lys
             60                  65                  70

Ala Cys Cys Val Pro Thr Lys Leu Ser Pro Ile Ser Val Leu Tyr Lys
             75                  80                  85

Asp Asp Met Gly Val Pro Thr Leu Lys Tyr His Tyr Glu Gly Met Ser
             90                  95                 100

Val Ala Glu Cys Gly Cys Arg
            105         110
```

(2) INFORMATION FOR SEQ ID NO:10:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:10:

```
ATCGGGCCCC TTTTAGCCAG GCGGAAAAGG AG                            32
```

(2) INFORMATION FOR SEQ ID NO:11:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:11:

```
AGCGAATTCC CCGCAGGCAG ATACTACCTG                               30
```

(2) INFORMATION FOR SEQ ID NO:12:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:12:

```
GATTCCGTCG ACCACCATGT CCCCTGGGGC CTGGTCTAGA TGGATACACA GCTGTGGGGC    60
C                                                                    61
```

(2) INFORMATION FOR SEQ ID NO:13:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:13:

```
CCACAGCTGT GTATCCATCT AGACCAGGCC CCAGGGGACA TGGTGGTCGA CG            52
```

```
(2) INFORMATION FOR SEQ ID NO:14:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:14:

GATTCCGTCG ACCACCATGT CCCCTGGGGC CTGGTCTAGA TGGATACACA GCTGTGGGGC     60

C                                                                    61

(2) INFORMATION FOR SEQ ID NO:15:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:15:

GCAGCTGGTG GTACAGGGGA CCCCGGACCA GATCTACCTA TGTGTCGACA CC             52

(2) INFORMATION FOR SEQ ID NO:16:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:16:

TCGACCACCA TGTCCCCTGG                                                 20

(2) INFORMATION FOR SEQ ID NO:17:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:17:

GCCCCAGGGG ACATGGTGG                                                  19

(2) INFORMATION FOR SEQ ID NO:18:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:18:
```

```
-continued

TCGACCACCA TGTCCCCTGG                                              20

(2) INFORMATION FOR SEQ ID NO:19:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:19:

GGTGGTACAG GGGACCCCG                                               19
```